US012577568B2

(12) United States Patent
Sullenger et al.

(10) Patent No.: US 12,577,568 B2
(45) Date of Patent: Mar. 17, 2026

(54) METHODS FOR CONTROLLING EXTRACORPOREAL MEMBRANE OXYGENATION (ECMO) COAGULATION

(71) Applicant: Duke University, Durham, NC (US)

(72) Inventors: Bruce Sullenger, Durham, NC (US); Elisabeth Tracy, Durham, NC (US); Christopher Reed, Durham, NC (US)

(73) Assignee: Duke University, Durham, NC (US)

( * ) Notice: Subject to any disclaimer, the term of this patent is extended or adjusted under 35 U.S.C. 154(b) by 918 days.

(21) Appl. No.: 17/782,848

(22) PCT Filed: Dec. 4, 2020

(86) PCT No.: PCT/US2020/063389
§ 371 (c)(1),
(2) Date: Jun. 6, 2022

(87) PCT Pub. No.: WO2021/113696
PCT Pub. Date: Jun. 10, 2021

(65) Prior Publication Data
US 2023/0012024 A1 Jan. 12, 2023

Related U.S. Application Data

(60) Provisional application No. 62/943,304, filed on Dec. 4, 2019.

(51) Int. Cl.
| | |
|---|---|
| *C12N 15/115* | (2010.01) |
| *A61K 47/54* | (2017.01) |
| *A61K 47/60* | (2017.01) |
| *A61P 7/02* | (2006.01) |

(52) U.S. Cl.
CPC .......... *C12N 15/115* (2013.01); *A61K 47/549* (2017.08); *A61K 47/60* (2017.08); *A61P 7/02* (2018.01); *C12N 2310/16* (2013.01); *C12N 2310/351* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 5,670,637 | A | 9/1997 | Gold et al. |
| 5,854,038 | A | 12/1998 | Sullenger et al. |
| 7,300,922 | B2 | 11/2007 | Sullenger et al. |
| 7,304,041 | B2 | 12/2007 | Rusconi |
| 7,312,325 | B2 | 12/2007 | Sullenger et al. |
| 7,396,664 | B2 | 7/2008 | Daly et al. |
| 7,566,701 | B2 | 7/2009 | Diener et al. |
| 7,741,307 | B2 | 6/2010 | Sullenger et al. |
| 7,776,836 | B2 | 8/2010 | Sullenger et al. |
| 8,367,627 | B2 | 2/2013 | Sullenger et al. |
| 8,790,924 | B2 | 7/2014 | Sullenger et al. |
| 9,061,043 | B2 | 6/2015 | Sullenger et al. |
| 9,340,591 | B2 | 5/2016 | Sullenger et al. |
| 9,687,529 | B2 | 6/2017 | Sullenger et al. |
| 9,873,727 | B2 | 1/2018 | Sullenger et al. |
| 11,634,772 | B2 | 4/2023 | Sullenger et al. |
| 2003/0083294 | A1 | 5/2003 | Sullenger et al. |
| 2003/0175703 | A1 | 9/2003 | Sullenger et al. |
| 2005/0176940 | A1 | 8/2005 | King |
| 2006/0040881 | A1 | 2/2006 | Rusconi |
| 2006/0264369 | A1 | 11/2006 | Diener et al. |
| 2009/0048193 | A1 | 2/2009 | Rusconi et al. |
| 2011/0197292 | A1 | 8/2011 | Sullenger et al. |
| 2012/0040373 | A1 | 2/2012 | Ubeda |
| 2012/0149764 | A1 | 6/2012 | Diener |
| 2014/0275226 | A1 | 9/2014 | Sullenger et al. |
| 2015/0247147 | A1 | 9/2015 | Rusconi |
| 2015/0322425 | A1 | 11/2015 | Sullenger et al. |
| 2017/0037544 | A1 | 2/2017 | Sullenger et al. |
| 2018/0117182 | A1 | 5/2018 | Sullenger et al. |
| 2020/0095636 | A1 | 3/2020 | Sullenger et al. |
| 2020/0283773 | A1 | 9/2020 | Sullenger et al. |
| 2020/0353102 | A1 | 11/2020 | Sullenger et al. |
| 2021/0308105 | A1* | 10/2021 | Steiner .................... A61P 31/14 |

FOREIGN PATENT DOCUMENTS

| | | | |
|---|---|---|---|
| WO | 1991019813 | 12/1991 | |
| WO | 2007035532 | 3/2007 | |
| WO | WO-2007140000 A2 * | 12/2007 | ............. A61K 31/00 |

OTHER PUBLICATIONS

Helms et al. J Throm Haemost. 21: pp. 373-396 (Year: 2023).*
Netley et al. J Extra Corpor Technol Sep. 2018;50:161-6 (Year: 2018).*
Ang et al. Blood transfusion requirements and independent predictors of increased transfusion requirements among adult patients on extracorporeal membrane oxygenation—a single centre experience. Vox Sanguinis, Jan. 2009; 96(1):34-43.
Arepally. Heparin-induced thrombocytopenia. Blood. May 2017;129(21):2864-2872.
Bagge et al. Low-molecular-weight heparin (Fragmin) versus heparin for anticoagulation during cardiopulmonary bypass in open heart surgery, using a pig model. Blood Coagulation & Fibrinolysis. Apr. 1994;5(2):265-272.
Barbaro et al. Pediatric Extracorporeal Life Support Organization Registry International Report 2016. ASAIO Journal. Jul./Aug. 2017; 63(4):456-463.
Bartlett et al. Initial ELSO Guidance Document: ECMO for COVID-19 Patients with Severe Cardiopulmonary Failure. ASAIO Journal. May 2020;66(5):472-474.

(Continued)

*Primary Examiner* — Brian Whiteman
(74) *Attorney, Agent, or Firm* — Quarles & Brady, LLP

(57) ABSTRACT
The present application provides for a method for controlling coagulation in a subject in need of extracorporeal membrane oxygenation. The method comprises administering an effective amount of an anticoagulant agent that directly inhibits one or more steps in a coagulation pathway to the subject, wherein the effective amount of the anticoagulant agent is capable of controlling coagulation during extra corporeal membrane oxygenation for a coagulation control time of at least 4 hours.

15 Claims, 19 Drawing Sheets
Specification includes a Sequence Listing.

(56) References Cited

OTHER PUBLICATIONS

Bateman et al. Anemia, blood loss, and blood transfusions in North American children in the intensive care unit. Am Journal of Respir Crit Care Med. Jul. 2008;178(1):26-33.

Bel et al. Inhibition of factor IXa by the pegnivacogin system during cardiopulmonary bypass: a potential substitute for heparin. A study in baboons. European Journal of Cardio-Thoracic Surgery. Feb. 2015;49(2):682-689.

Bompiani et al. Probing the coagulation pathway with aptamers identifies combinations that synergistically inhibit blood clot formation. Chemistry & Biology. Aug. 2014;21(8):935-944.

Buddai et al. An anticoagulant RNA aptamer that inhibits proteinase-cofactor interactions within prothrombinase. Journal of Biological Chemistry. Feb. 2010;285(8):5212-5223.

Cashen et al. Platelet Transfusion Practice and Related Outcomes in Pediatric Extracorporeal Membrane Oxygenation. Pediatr Crit Care Med. Feb. 2020;21(2):178-185.

Chabata et al. Emerging applications of aptamers for anticoagulation and hemostasis. Curr Opin Hematol. Sep. 2018;25(5):382-388.

Chan et al. A randomized, repeat-dose, pharmacodynamic and safety study of an antidote-controlled factor IXa inhibitor. Journal of Thrombosis & Haemostasis. May 2008;6(5):789-796.

Chan et al. Phase 1b randomized study of antidote-controlled modulation of factor IXa activity in patients with stable coronary artery disease. Circulation. Jun. 2008;117(22):2865-2874.

Dyke et al. First-in-human experience of an antidote-controlled anticoagulant using RNA aptamer technology: a phase 1a pharmacodynamic evaluation of a drug-antidote pair for the controlled regulation of factor IXa activity. Circulation. Dec. 2006;114(23):2490-2497.

European Patent Office, Extended European Search Report for EP Application 20896722.4 mailed Jul. 29, 2024. 12 pages.

Extracorporeal Life Support Organization (ELSO). ECLS Registry Report—International Summary. Jul. 2019. Accessed Nov. 11, 2019, from https://www.elso.org/Registry/Statistics/InternationalSummary.aspx.

Gaffney et al. Extracorporeal life support. BMJournal. Nov. 2010;341:c5317.

Gopinath et al. A potent anti-coagulant RNA aptamer inhibits blood coagulation by specifically blocking the extrinsic clotting pathway. Thrombosis and Haemostasis. 2006;95(5):767-771.

Groenen et al. Analyses of pig genomes provide insight into porcine demography and evolution. Nature. Nov. 2012;491(7424):393-398.

Gunaratne et al. Combination of aptamer and drug for reversible anticoagulation in cardiopulmonary bypass. Nature Biotechnology. Aug. 2018;36(7):606-613.

Helms et al. High risk of thrombosis in patients with severe SARS-CoV-2 infection: a multicenter prospective cohort study. Intensive Care Med. Jun. 2020;46(6):1089-1098.

Heman-Ackah et al. Neurologically Devastating Intraparenchymal Hemorrhage in COVID-19 Patients on Extracorporeal Membrane Oxygenation: A Case Series. Neurosurgery. Aug. 2020;87(2):E147-E151.

Hoffman et al. Factors IXa and Xa play distinct roles in tissue factor-dependent initiation of coagulation. Blood. 1995;86(5):1794-1801.

International Searching Authority, International Search Report and Written Opinion for International Patent Application No. PCT/US2020/063389, dated Mar. 23, 2021. 11 pages.

Jacobs et al. Extracorporeal Membrane Oxygenation in the Treatment of Severe Pulmonary and Cardiac Compromise in Coronavirus Disease 2019: Experience with 32 Patients. ASAIO Journal. Jul. 2020;66(7):722-730.

Klok et al. Confirmation of the high cumulative incidence of thrombotic complications in critically ill ICU patients with COVID-19: An updated analysis. Thrombosis Research. Jul. 2020;191:148-150.

Köstering et al. Blood coagulation studies in domestic pigs (Hanover breed) and minipigs (Goettingen breed). Laboratory Animals. 1983;17(4):346-349.

Kuhle et al. Lack of correlation between heparin dose and standard clinical monitoring tests in treatment with unfractionated heparin in critically ill children. Haematologica. Apr. 2007;92(4):554-557.

Kurundkar et al. Extracorporeal membrane oxygenation causes loss of intestinal epithelial barrier in the newborn piglet. Pediatr Res. Aug. 2010;68(2):128-133.

Larsson et al. A factor XIIa inhibitory antibody provides thromboprotection in extracorporeal circulation without increasing bleeding risk. Sci Transl Med. Feb. 2014;6(222):222ra17.

Layzer and Sullenger. Simultaneous generation of aptamers to multiple gamma-carboxyglutamic acid proteins from a focused aptamer library using DeSELEX and convergent selection. Oligonucleotides. Mar. 2007;17(1):1-11.

Lelovas et al. A comparative anatomic and physiologic overview of the porcine heart. Journal of Am Assoc Lab Anim Sci. Sep. 2014;53(5):432-438.

Lequier et al. ELSO Anticoagulation Guideline. 2014. Accessed Apr. 6, 2020, from: https://www.elso.org/portals/0/files/elsoanticoagulationguideline8-2014-table-contents.pdf.

Levy et al. Antithrombin: anti-inflammatory properties and clinical applications. Thrombosis and Haemostasis. 2016;115(4):712-728.

Lunney. Advances in swine biomedical model genomics. Int Journal of Biol Sci. Feb. 2007;3(3):179-184.

Maclaren et al. Preparing for the Most Critically Ill Patients With COVID-19: The Potential Role of Extracorporeal Membrane Oxygenation. JAMA. Apr. 2020;323(13):1245-1246.

Makdisi and Wang. Extra Corporeal Membrane Oxygenation (ECMO) review of a lifesaving technology. Journal of Thorac Dis. 2015;7(7):E166-E176.

Massicotte et al. A comparative study of coagulation systems in newborn animals. Pediatr Res. 1986;20(10):961-965.

May et al. FXIIa inhibitor rHA-Infestin-4: Safe thromboprotection in experimental venous, arterial and foreign surface-induced thrombosis. Br Journal of Haematol. Jun. 2016;173(5):769-778.

Millar et al. The inflammatory response to extracorporeal membrane oxygenation (ECMO): a review of the pathophysiology. Crit Care. Dec. 2016;20(1):387.

Mittermayr et al. Effects of protamine and heparin can be detected and easily differentiated by modified thrombelastography (Rotem): an in vitro study. Br Journal of Anaesth. 2005;95(3):310-316.

Mohankumar et al. Intestinal epithelial apoptosis initiates gut mucosal injury during extracorporeal membrane oxygenation in the newborn piglet. Lab Invest. 2014;94(2):150-160.

Münster et al. Usefulness of human coagulation and fibrinolysis assays in domestic pigs. Comp Med. Feb. 2002;52(1):39-43.

National Institutes of Health (NIH). Coronavirus Disease 2019 (COVID-19) Treatment Guidelines: Extracorporeal Membrane Oxygenation. Apr. 2020. Accessed Jun. 21, 2020, from https://covid19treatmentguidelines.nih.gov/critical-care/extracorporeal-membrane-oxygenation/.

Nellenbach et al. Comparison of Neonatal and Adult Fibrin Clot Properties between Porcine and Human Plasma. Anesthesiology. May 2020;132(5):1091.

Nimjee et al. A novel antidote-controlled anticoagulant reduces thrombin generation and inflammation and improves cardiac function in cardiopulmonary bypass surgery. Mol Ther. Sep. 2006;14(3):408-415.

Nimjee et al. Aptamers as Therapeutics. Annu Rev Pharmacol Toxicol. Jan. 2017;57(1):61-79.

Nimjee et al. Preclinical Development of a vWF Aptamer to Limit Thrombosis and Engender Arterial Recanalization of Occluded Vessels. Mol Ther. Jul. 2019;27(7):1228-1241.

Nimjee et al. Translation and Clinical Development of Antithrombotic Aptamers. Nucleic Acid Ther. Jun. 2016;26(3):147-155.

Noubouossie et al. Red blood cell microvesicles activate the contact system, leading to factor IX activation via 2 independent pathways. Blood. 2020;135(10):755-765.

Nugent. Heparin sequencing brings structure to the function of complex oligosaccharides. Proc Natl Acad Sci U S A. Sep. 2000;97(19):10301-10303.

(56)　　　　　References Cited

OTHER PUBLICATIONS

Olsen et al. The pig as a model in blood coagulation and fibrinolysis research. Scandinavian Journal of Laboratory Animal Sciences. Dec. 1999;26(4):10.

Oney et al. Development of universal antidotes to control aptamer activity. Nature Medicine. Oct. 2009;15(10):1224-1228.

Ontaneda and Annich. Novel Surfaces in Extracorporeal Membrane Oxygenation Circuits. Frontiers in Medicine (Lausanne). Nov. 2018;5:321.

Paden et al. Extracorporeal Life Support Organization Registry Report 2012. ASAIO Journal. May 2013;59(3):202-210.

Pfohler et al. Delayed-type heparin allergy: diagnostic procedures and treatment alternatives-a case series including 15 patients. World Allergy Organ Journal. Dec. 2008;1(12):194-199.

Pireaux et al. Anticoagulation With an Inhibitor of Factors XIa and XIIa During Cardiopulmonary Bypass. Journal of Am Coll Cardiol. Oct. 2019;74(17):2178-2189.

Reed et al. Aptamer-based factor IXa inhibition preserves hemostasis and prevents thrombosis in a piglet model of ECMO, Molecular Therapy-Nucleic Acids. 2022;27:524-534.

Reed et al. Coagulopathy Characterized by Rotational Thromboelastometry in a Porcine Pediatric ECMO Model. Journal of Extra Corpor Technol. Sep. 2020;52(3):203-211.

Rusconi et al. RNA aptamers as reversible antagonists of coagulation factor IXa. Nature. Sep. 2002;419(6902):90-94.

Sanfilippo et al. Bivalirudin for Alternative Anticoagulation in Extracorporeal Membrane Oxygenation: A Systematic Review. Journal of Intensive Care Med. Jun. 2017;32(5):312-319.

Schindelin et al. Fiji: an open-source platform for biological-image analysis. Nature Methods. Jul. 2012;9(7):676-682.

Slaughter et al. HeartWare ventricular assist system for bridge to transplant: combined results of the bridge to transplant and continued access protocol trial. Journal of Heart Lung Transplant. Jul. 2013;32(7):675-683.

Stafford. Extravascular FIX and coagulation. Thrombosis Journal. 2016;14(Suppl 1):35.

Stern et al. In vivo evidence of intravascular binding sites for coagulation factor IX. British Journal of Haematology. Jun. 1987;66(2):227-232.

Sullenger et al. Potent anticoagulant aptamer directed against factor IXa blocks macromolecular substrate interaction. Journal of Biol Chem. Apr. 2012;287(16):12779-12786.

Sutter et al. Acute Neurologic Complications During Extracorporeal Membrane Oxygenation: A Systematic Review. Crit Care Med, Sep. 2018;46(9):1506-1513.

Sy et al. Anticoagulation practices and the prevalence of major bleeding, thromboembolic events, and mortality in venoarterial extracorporeal membrane oxygenation: A systematic review and meta-analysis. Journal of Crit Care. Jun. 2017;39:87-96.

Tanaka et al. In-vitro evaluation of anti-factor IXa aptamer on thrombin generation, clotting time, and viscoelastometry. Thrombosis and Haemostasis. 2009; 101(05):827-833.

Tang et al. Abnormal coagulation parameters are associated with poor prognosis in patients with novel coronavirus pneumonia. Journal of Thrombosis and Haemostasis. Apr. 2020;18(4):844-847.

Toulon et al. Age dependency for coagulation parameters in paediatric populations. Results of a multicentre study aimed at defining the age-specific reference ranges. Thrombosis and Haemostasis. 2016;116(07):9-16.

Tuerk and Gold, Systematic evolution of ligands by exponential enrichment: RNA ligands to bacteriophage T4 DNA polymerase. Science. Aug. 1990;249(4968):505-510.

Walchak et al. Simple blood typing and cross matching techniques in swine. Lab Anim (NY). Oct. 2016;45(10):366-368.

Walker and Royston. Thrombin generation and its inhibition: a review of the scientific basis and mechanism of action of anticoagulant therapies. Br Journal of Anaesth. Jun. 2002;88(6):848-863.

Werho et al. Hemorrhagic complications in pediatric cardiac patients on extracorporeal membrane oxygenation: an analysis of the Extracorporeal Life Support Organization Registry. Pediatr Crit Care Med. Mar. 2015;16(3):276-288.

Woodruff et al. Generation and characterization of aptamers targeting factor XIa. Thromb Res. Aug. 2017;156:134-141.

Woodruff et al. Inhibiting the intrinsic pathway of coagulation with a factor XII-targeting RNA aptamer. Journal of Thrombosis and Haemostasis. Jul. 2013;11(7):1364-1373.

Woodruff et al. The many faces of the contact pathway and their role in thrombosis. Journal of Thrombosis and Thrombolysis. Jul. 2011;32(1):9-20.

Xanthos et al. Baseline hemodynamics in anesthetized landrace-large white swine: reference values for research in cardiac arrest and cardiopulmonary resuscitation models. Journal of Am Assoc Lab Anim Sci. Sep. 2007;46(5):21-25.

* cited by examiner

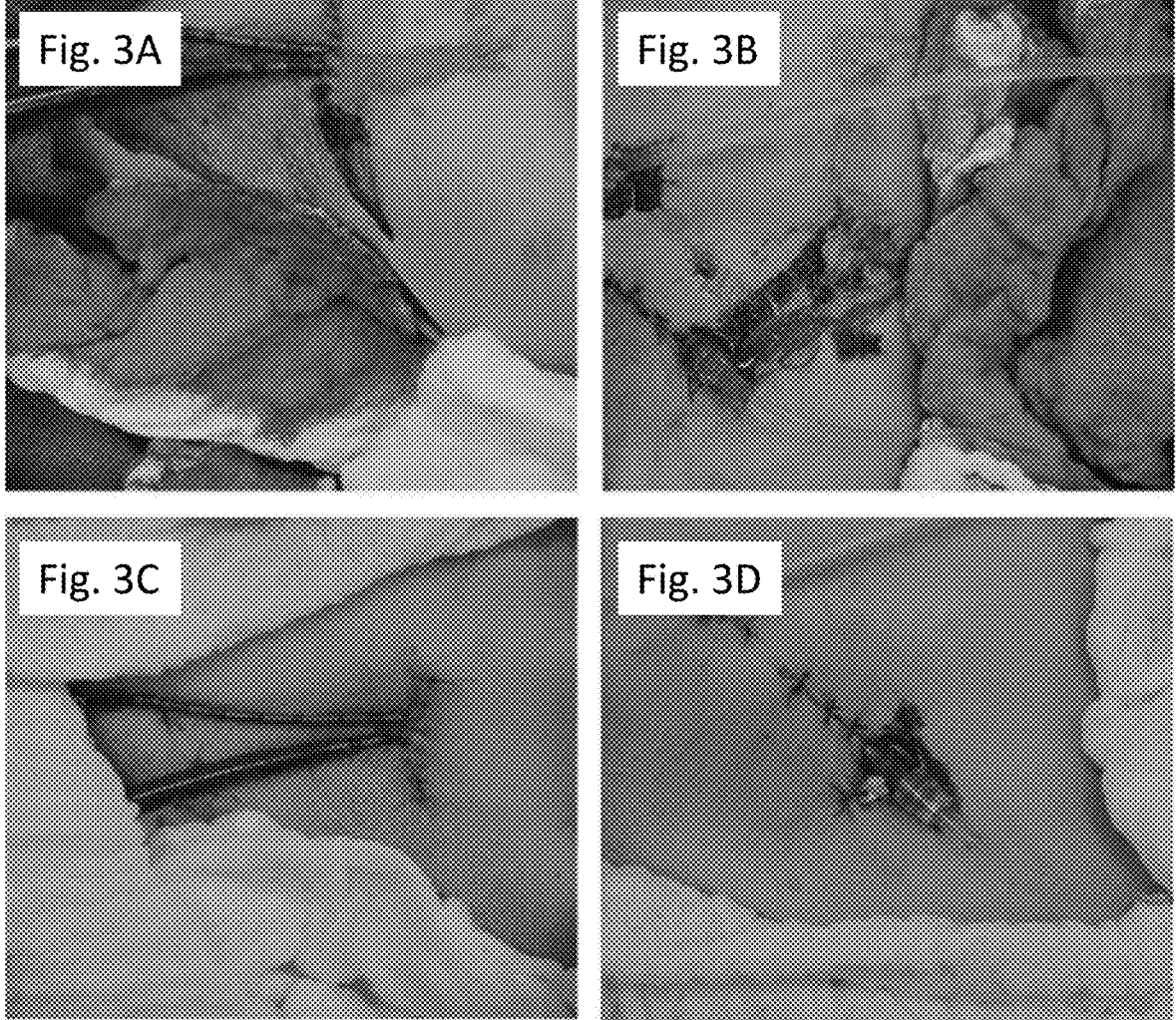

Fig. 3E

Heparin

Heparin Lab Draw Volume

DTRI-178

DTRI-178 Lab Draw Volume

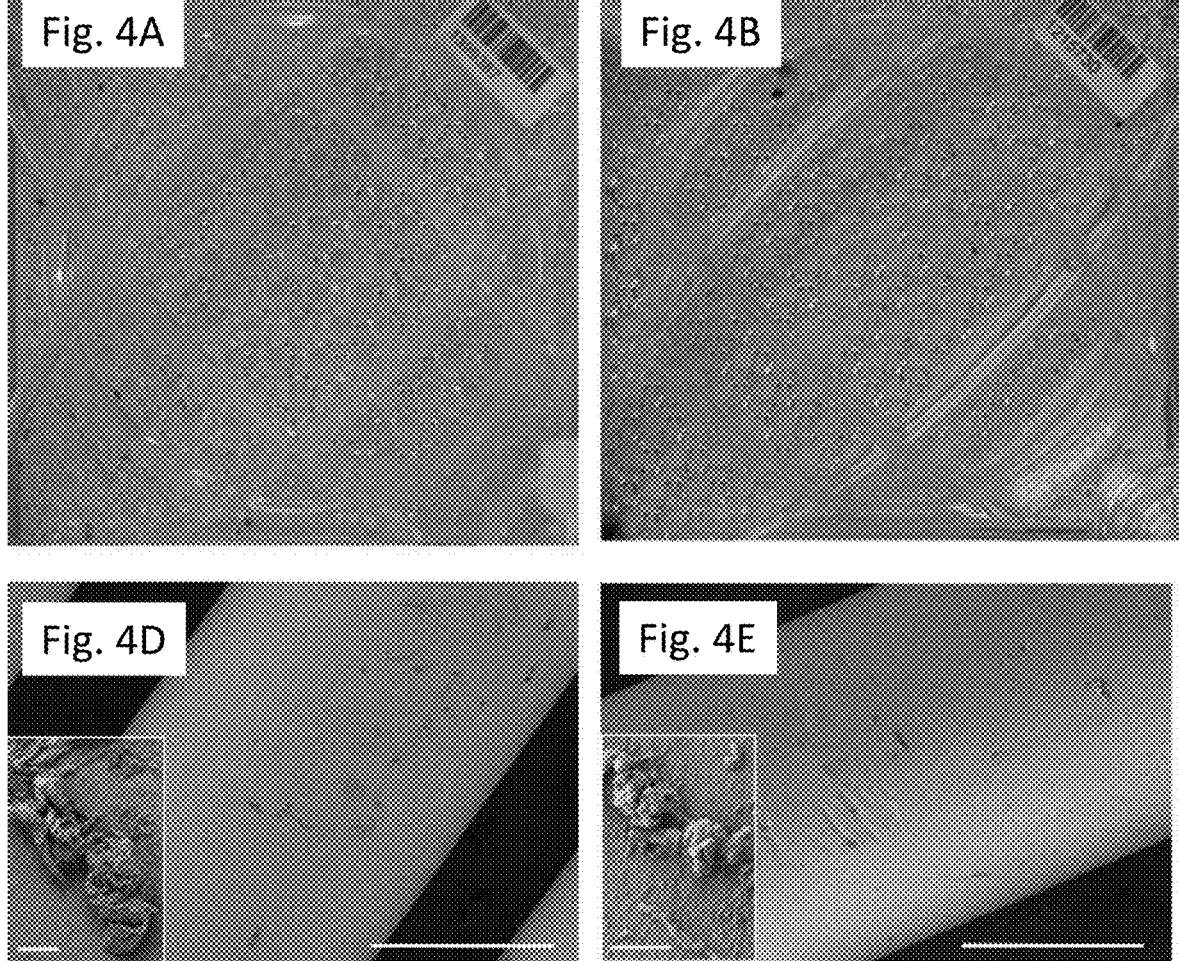

DTRI-178 Concentration (µm)

METHODS FOR CONTROLLING EXTRACORPOREAL MEMBRANE OXYGENATION (ECMO) COAGULATION

CROSS-REFERENCE TO RELATED APPLICATIONS

The present application is a national stage filing under 35 U.S.C. § 371 of International Patent Application No. PCT/US2020/063389, filed Dec. 4, 2020, which claims the benefit of priority to U.S. Provisional Patent Application No. 62/943,304, that was filed Dec. 4, 2019, the entire contents of which are all hereby incorporated by reference in their entirety.

STATEMENT REGARDING FEDERALLY SPONSORED RESEARCH

This invention was made with government support under Grant No. HL0652222 awarded by the National Institutes of Health. The government has certain rights in the invention.

REFERENCE TO A SEQUENCE LISTING

This application is being filed electronically via EFS-Web and includes an electronically submitted Sequence Listing in .txt format. The .txt file contains a sequence listing entitled "155554_00575_ST25.txt" created on Dec. 2, 2020 and is 975 bytes in size. The Sequence Listing contained in this .txt file is part of the specification and is hereby incorporated by reference herein in its entirety.

BACKGROUND OF THE INVENTION

Venoarterial (VA) extracorporeal membrane oxygenation (ECMO) is an ex vivo temporary cardiopulmonary support procedure that may be used to support heart and lung functions for days, weeks, or months. Venous and arterial cannulae, polyvinylchloride (PVC) tubing segments, and a mechanical pump are utilized to channel central venous blood through a membrane oxygenator, through a heat exchanger, and then into the patient's arterial system. The analogous but less invasive procedure venovenous (VV) ECMO returns oxygenated blood to the patient's central venous system to support oxygenation without cardiac augmentation.

During ECMO, systemic anticoagulation is necessary to prevent coagulation that would otherwise be triggered when the patient's blood contacts the surfaces of the ECMO circuit. Unfractionated heparin (UFH) is the standard anticoagulant used in ECMO and has numerous important drawbacks which arise from its origin, composition, structure, anticoagulation mechanisms, and immunogenicity. The most overt, common, and perhaps important adverse effect of unfractionated heparin (UFH) infusion on ECMO is bleeding. Strategies aimed at reducing heparin exposure and mitigating hemorrhagic risk, such as platelet transfusions and improving biocompatibility of synthetic circuit components, do not obviate the need for systemic anticoagulation and associated effects of UFH.

Infants and children are at particularly high risk for hemorrhagic complications while on ECMO. UFH infusion can be particularly problematic in newborns, in whom AT circulates at a concentration less than 50% of its concentration in healthy adults. Their smaller circulating blood volume necessitates near-daily blood transfusions due to small-volume but ongoing blood loss (typically from cannulation sites). Intracranial hemorrhage is also six times more common in neonates compared to adults. Lastly, the immaturity of the neonatal hemostatic system also makes effective monitoring much more complicated and potentially morbid. Since AT exerts both anti-inflammatory and anticoagulant effects, the depletion of AT not only reduces UFH's efficacy, but may also exacerbate disease-related and ECMO-induced inflammation.

Another important complication of heparin therapy that is particularly prevalent among adults is development of heparin-induced thrombocytopenia (HIT), an immune response that develops in 1-3% of patients who receive prolonged UFH infusions. If unrecognized, HIT can cause end-organ damage and life-threatening thrombosis.

In addition, UFH does not effectively inhibit thrombin generation during ECMO or CPB and cannot inactivate clot bound thrombin. These limitations can result in the depletion of prothrombin and the activation of inflammation in these settings.

These procedures are lifesaving for many infants with primary pulmonary hypertension, meconium aspiration, congenital diaphragmatic hernia, and other congenital anomalies; as well as for many adults and older children with acute respiratory distress syndrome (ARDS) consequent to critical illness, trauma and viral infections. ECMO is also used to provide circulatory support following cardiac arrest. Recently, VV (and, less commonly, VA) ECMO has been used for refractory hypoxemia in severe COVID-19 pneumonia, and may be considered as a supportive therapy when other options have been exhausted. Published experience with ECMO in the treatment of patients with severe COVID-19 ECMO is still emerging, but thrombophilia associated with the illness presents a challenge in ICU management. For example, in one large multicenter study, nearly 100% of patients requiring renal replacement therapy clotted the circuit. Coagulopathic or hemorrhagic complications were cited as the cause of 30% of deaths among COVID-19 patients on ECMO in one series. A more suitable anticoagulant would prevent thrombosis but not induce hemorrhage in this vulnerable population.

BRIEF SUMMARY OF THE INVENTION

Disclosed herein are methods for controlling coagulation in subjects in need of extracorporeal membrane oxygenation. One aspect of the invention provides for a method for controlling coagulation in a subject in need of extracorporeal membrane oxygenation. The method may comprise administering an effective amount of an anticoagulant agent that directly inhibits one or more steps in a coagulation pathway to the subject, wherein the effective amount of the anticoagulant agent is capable of controlling coagulation during extra corporeal membrane oxygenation for a coagulation control time of at least 4 hours. In some embodiments, the method further comprises administering a second effective amount of the anticoagulant agent to the subject after the coagulation control time. In some embodiments, wherein the subject does not receive an administration of the anticoagulant agent during the coagulation control time. In some embodiments, the second effective amount of the anticoagulant agent is administered as a bolus.

Another aspect of the invention provides for a method for controlling coagulation in a subject in need of extracorporeal membrane oxygenation. The method may comprise administering an effective amount of an anticoagulant agent that directly inhibits one or more steps in a coagulation pathway to the subject and monitoring the subject for an indication of coagulation after the anticoagulation control time, wherein the effective amount of the anticoagulant agent is capable of controlling coagulation during extracorporeal membrane oxygenation for a coagulation control time of at least 4 hours. In some embodiments, the subject is not monitored for an indication of coagulation during the coagulation control time.

Another aspect of the invention provides for a method for selecting a subject for anticoagulant agent therapy. The method may comprise determining whether the subject has hypersensitivity to an anticoagulant agent or a component thereof and administering an effective amount of the anticoagulant agent to a subject lacking hypersensitivity to the anticoagulant agent or the component thereof. In some embodiments, the effective amount of the anticoagulant agent is capable of controlling coagulation during extracorporeal membrane oxygenation for a coagulation control time of at least 4 hours. In some embodiments, hypersensitivity to the anticoagulant agent is determined by administering the anticoagulant agent by skin, oral, or nasal challenge. In other embodiments, hypersensitivity to the anticoagulant agent is determined by screening the subject for antibodies indicative of hypersensitivity to the anticoagulant agent or a component thereof.

Another aspect of the invention provides for a method for controlling coagulation in a subject in need of extracorporeal membrane oxygenation, the method comprising administering an effective amount of an anticoagulant aptamer that directly inhibits one or more coagulation factors or an activated form thereof in the coagulation system of the subject, wherein the effective amount of the anticoagulant agent is capable of controlling coagulation during extracorporeal membrane oxygenation for a coagulation control time of at least 4 hours. In some embodiments, the anticoagulant aptamer is PEGylated. In some embodiments, wherein the anticoagulant aptamer comprises an oligonucleotide having at least 80% sequence identity to any one of SEQ ID NOS: 1-3. In a particular embodiments, the anticoagulant aptamer comprises the oligonucleotide of SEQ ID NO: 1.

In some embodiments, the anticoagulation control time is at least 6 hours, at least 8 hours, at least 10 hours, or at least 12 hours. In some embodiments, the anticoagulation control time is characterized by one or more of the following: hematocrit stability, absence of a need for blood transfusion, clinical evidence of hemostasis, absence of clinical signs of bleeding, negligible extracorporeal transmembrane oxygenator pressure gradient, or stable blood flows through the extracorporeal membrane oxygenator.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

(FIG. 2A) ECMO flow was measured hourly by a flow transducer immediately post-oxygenator. Each individual animal's measurements are connected by line segments. (FIG. 2B) Transmembrane oxygenator pressure gradient ($\Delta P$) was measured hourly by subtracting the hydrostatic pressure measured at the oxygenator outflow from the inflow. The clinically relevant normal and critical upper limit pressures are indicated with dashed lines. Each individual animal's measurements are connected by line segments.

Figure 3E:
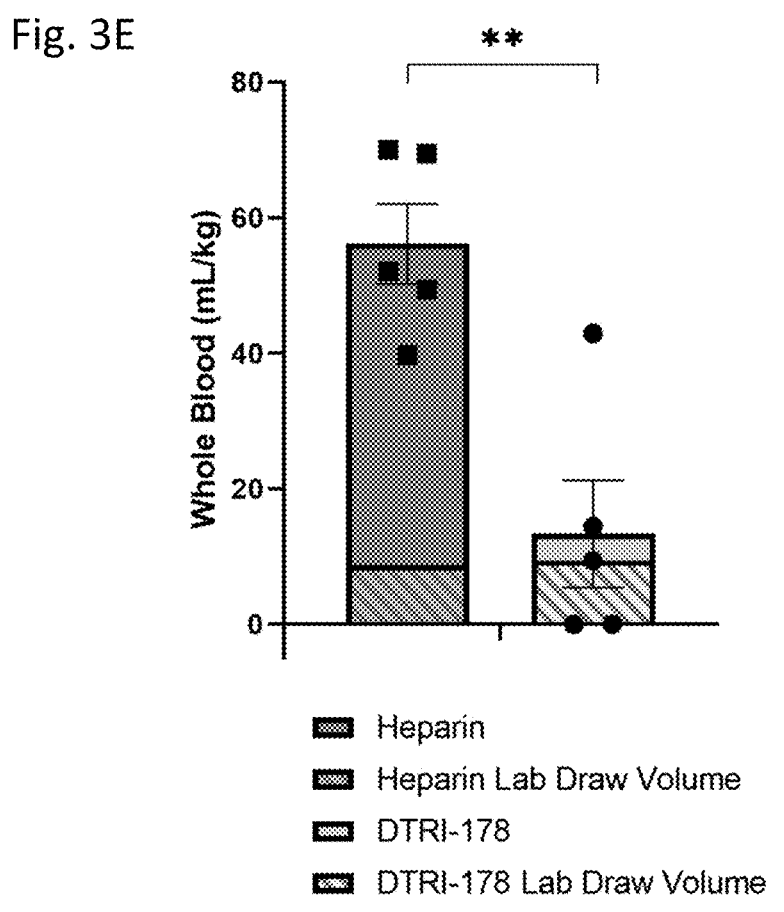

FIGS. 3A-3E show Blood transfusion volumes and clinical bleeding events. FIGS. 3A-3D) Clinical bleeding at the experiment completion (12 hr total) at the sites of cannulation at neck (FIG. 3A, 3C) and instrumentation at groin (FIG. 3B, 3D). Representative photos of heparinized (top: FIG. 3A, 3B) and DTRI-178-treated (bottom: FIG. 3C, 3D) animals are provided. (FIG. 3E) Whole blood transfusion volume. Individual points are transfusion totals in mL/kg. Bars represent the mean transfusion totals and error bars are standard error of the mean. Striped boxes represent the estimated total blood volume removed throughout the run for study sampling and monitoring.

FIGS. 4A-4F show macroscopic inspection and scanning electron microscopy (SEM) analyses of clotting on membrane oxygenators. FIGS. 4A-4B are photographs of the median-clotted membrane oxygenator from (FIG. 4A) heparinized, and (FIG. 4B) DTRI-178-treated animals. (FIG. 4C) The percentage of total oxygenator surface area covered with clot, expressed as the mean±the standard error of the mean. Data points indicate value for all five animals in each group. (FIG. 4D-4E) Scanning electron micrographs of oxygenator fibers from the median-clotted (FIG. 4D) heparin and (FIG. 4E) DTRI-178-treated animals. Inlays are higher-magnification images of representative clots. Lower magnification=65×, inlays=1,500 and 2,500×, respectively. Scale bars at lower magnification=200 μm, inlays=10 μm. (FIG. 4F) The percentage of the total oxygenator surface area covered with clot, expressed as the mean±the standard error of the mean. Data points indicate the separate average values for fibers obtained from the superficial and deep portions of the oxygenators for three animals in each group.

(FIG. 6A) ROTEM EXTEM coagulation time (CT). The CT of the extrinsic pathway is unaffected by the addition of either heparin (red) or DTRI-178 (turquoise). (FIG. 6B) ROTEM HEPTEM CT for heparin animals and INTEM CT for DTRI-178 animals. As expected, CT is prolonged among aptamer-treated animals immediately after administration. CT remains near normal among heparinized animal due to the effects of the HEPTEM test pre-treatment, which neutralizes heparin's effects on the CT in order to demonstrate underlying coagulopathy. (FIG. 6C) ROTEM EXTEM maximum clot firmness (MCF). The overall clot firmness remains unchanged and similar between study groups. (FIG. 6D) ROTEM HEPTEM MCF for heparin animals and INTEM MCF for DTRI-178 animals. The overall clot firmness remains unchanged and similar between study groups. (FIG. 6E) ROTEM FIBTEM MCF. The acellular clot firmness (i.e., minus platelet contribution) is decreased after initiating ECMO, but is similar between groups and steady throughout the remainder of the experiment.

(FIG. 8A) EXTEM test (tissue factor activator) demonstrates no effect of DTRI-178 on coagulation time, analogous to the prothrombin time. (FIG. 8B) HEPTEM test (intrinsic coagulation cascade activator) demonstrates prolongation of the intrinsic coagulation time (CT), analogous to the activated partial thromboplastin time, after addition of DTRI-178 in both healthy and COVID-19 patient samples. (FIG. 8C) EXTEM test also demonstrates no effect of DTRI-178 on clot firmness. (FIG. 8D) HEPTEM test (intrinsic coagulation cascade activator) demonstrates no effect on maximum clot firmness in both buffer and DTRI-178 conditions. (FIG. 8E) FIBTEM test demonstrates no effect of DTRI-178 on clot firmness in an acellular clot (i.e., fibrin-only).

(FIG. 10A) PaO$_2$. (FIG. 10B) PaCO$_2$.

DETAILED DESCRIPTION OF THE INVENTION

Figure 1A:
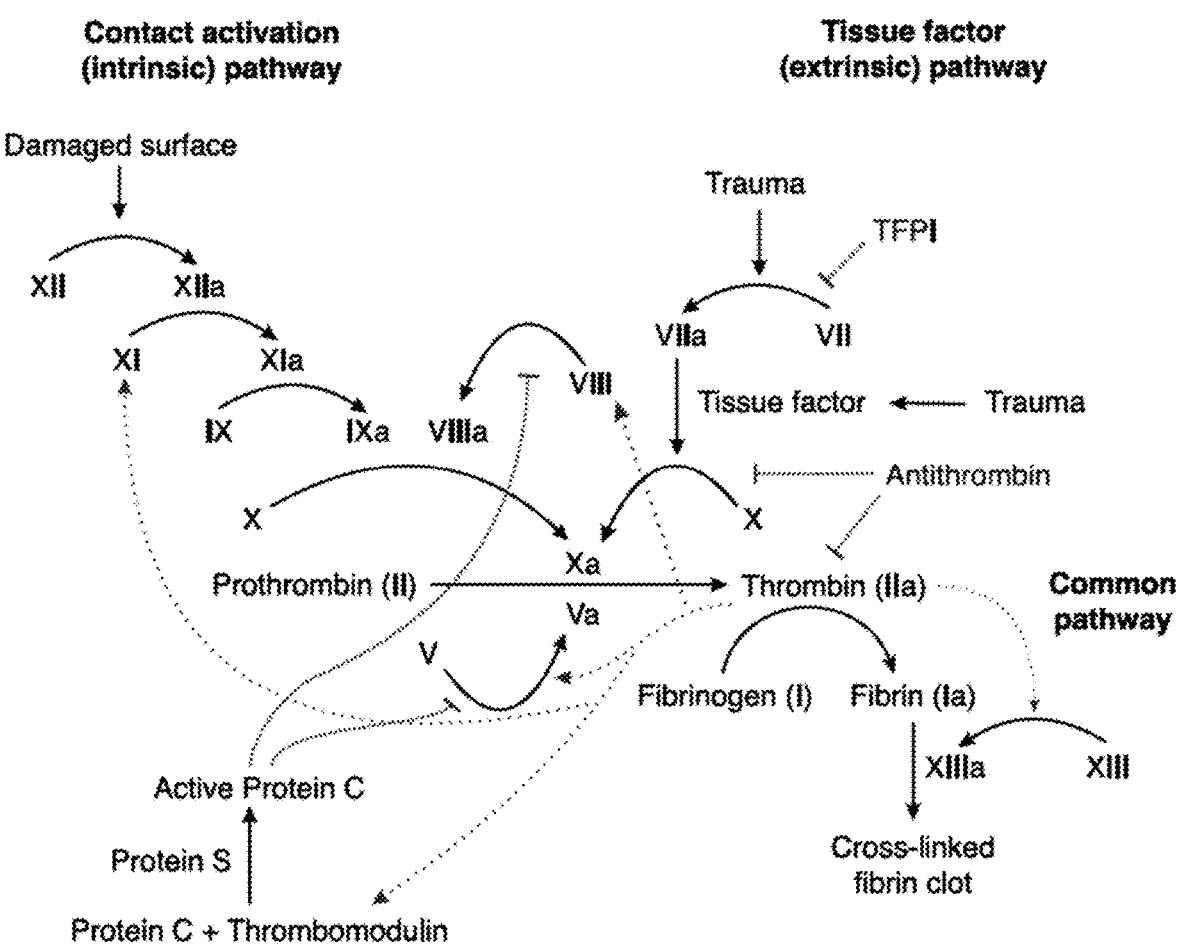
FIG. 1A shows a schematic of the coagulation pathway.

Disclosed herein are methods for controlling coagulation in subjects in need of extracorporeal membrane oxygenation. As demonstrated in the Examples that follow, the use of an anticoagulant aptamer that directly inhibits one or more steps in the coagulation system is capable of achieving thromboprevention of the subject during extended periods of extracorporeal membrane oxygenation. Thromboprevention with the anticoagulant aptamer was comparable to use of heparin, currently the standard of care. Surprisingly anticoagulation with the anticoagulant aptamer had reduced surgical site bleeding and reduced need for blood transfusion. Moreover, anticoagulant aptamers provided durable thromboprevention without the need for constant anticoagulant infusion; and reduced the monitoring burden and need for repetitive blood draws and transfusions.

One aspect of the invention provides for methods for controlling coagulation in a subject in need of extracorporeal membrane oxygenation. ECMO is an extracorporeal technique of providing prolonged cardiac and respiratory support to persons whose heart and lungs are unable to provide an adequate amount of gas exchange or perfusion to sustain life. ECMO works by temporarily drawing blood from the body to allow artificial oxygenation of the red blood cells and removal of carbon dioxide. ECMO is a treatment for subjects with profound heart and/or lung failure and allows for treatment of the underlying cause of heart and/or lung failure while circulation and oxygenation are supported. Exemplary clinical situations that may prompt the need for initiating ECMO include primary pulmonary hypertension, meconium aspiration, congenital diaphragmatic hernia, congenital anomalies of the cardiopulmonary system, hypoxemic respiratory failure, hypercapnic respiratory failure, refractory cardiogenic shock, cardiac arrest, failure to wean from cardiopulmonary bypass, septic shock, hypothermia, trauma, and acute respiratory distress syndrome or severe acute respiratory syndrome, amongst others. ECMO may also be used to support patients with the acute viral pneumonia or cardiopulmonary failure associated with COVID-19 in cases where artificial ventilation is not sufficient to sustain blood oxygenation levels.

As used herein, a "subject" may be interchangeable with "patient" or "individual" and means an animal, which may be a human or non-human animal, in need of treatment. A "subject in need of extracorporeal membrane oxygenation" may include a subject having a disease, disorder, or condition that is responsive to therapy with ECMO or prolonged cardiac or respiratory support.

As a consequence of ECMO, the subject is also in need of an anticoagulant agent, such as the anticoagulant aptamers described herein, to control coagulation during ECMO therapy. Accordingly, ECMO and an effective amount of anticoagulant agent are intended to be administered in combination. An anticoagulant agent directly inhibits one or more steps in a coagulation pathway or coagulation system. An anticoagulant agent that directly inhibits one or more steps of the coagulation pathway or the coagulation system may inhibit one or more proteins of the coagulation system by binding to a protein associate with the coagulation system such as a coagulation factor or an activated form thereof, thereby interfering with or arresting one of more steps of the pathway. Accordingly, the anticoagulant agent may be an anticoagulant aptamer or a composition comprising an anticoagulant aptamer.

As used herein the term "effective amount" refers to the amount or dose of the anticoagulant agent, upon single or multiple dose administration to the subject, which provides the desired effect in the subject under diagnosis or treatment. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

In some embodiments, the anticoagulant agent is administered to a subject lacking hypersensitivity to the anticoagulant agent or a component thereof. Hypersensitivity includes immediate and/or severe reaction to the anticoagulant agent, including without limitation anaphylaxis. Hypersensitivity can be readily determined by the attending clinician or diagnostician, as one skilled in the art, by the use of known techniques and by observing results obtained under analogous circumstances. Suitably, hypersensitivity may be determined for the anticoagulant agent by skin, oral, or nasal challenge or by screening the subject for antibodies indicative of hypersensitivity to the anticoagulant agent or a component thereof. In some embodiments, a subject may be hypersensitive to an aptamer or a biocompatible polymer, such as PEG, and screening may be used to eliminate subjects with a high likelihood for a severe adverse reaction to the anticoagulant agent.

In some embodiments, the anticoagulant agent is administered prior to initiation of ECMO. Because ECMO therapy is intended as a prolonged therapy to be used over the course of hours (e.g., 1, 2, 4, 6, 8, 10, 12, 14, 16, 18, 20, 22, or 24 hours), days (e.g., 1, 2, 3, 4, 5, 6, 7, 8, 9, 10, 11, 12, 13, 14, or more than 14 days) or weeks (e.g., 1, 2, 3, 4, or more than 4 weeks), it is typically necessary to re-administer an effective amount of the anticoagulant agent to control coagulation during these extended periods of ECMO therapy.

Coagulation control, or alternatively controlling coagulation, means that the subject has a clinically acceptable susceptibility to coagulation during ECMO therapy. A clinically acceptable susceptibility to coagulation during ECMO therapy can be readily determined by the attending clinician, as one skilled in the art, by the use of known techniques and by observing results obtained under analogous circumstances. Adequate coagulation control is assessed generally by a) laboratory monitoring and b) clinical signs of thrombosis and hemorrhage. In the case of a) laboratory monitoring, the conventional coagulation tests activated partial thromboplastin time (aPTT) and prothrombin time (PT) provide information on the length of time required to form a clot under controlled circumstances in vitro. The more physiologic viscoelastic hemostatic tests (i.e., rotational thromboelastometry and thromboelastography) may also be used. Finally, in the case of b) clinical signs of thrombosis and hemorrhage, clotting in the oxygenator of the ECMO circuit may cause increased resistance to flow that is measured during the run, and hemorrhage may manifest as diffuse bleeding from surgical and monitoring sites on the patient.

An advantage of the anticoagulant agents described herein is that the anticoagulant agents provide durable thrombo-prevention without the need for constant anticoagulant infusion and reduced monitoring burden. Accordingly, the effective amount of anticoagulant agent allows for coagulation control over extended periods of time. Suitably, the effective amount of anticoagulant agent may provide for at least 1 hour of coagulation control. In some embodiments, the effective amount anticoagulant agent provides for at least 2, 4, 6, 8, 10, 12, or more than 12 hours of coagulation control time.

In some embodiments, the subject is administered successive administrations of the anticoagulant agent separated by at least the coagulation control time. Suitably the time between administrations may be separated by at least 1 hour, including least 2, 4, 6, 8, 10, 12, or more than 12 hours. In some embodiments one or both of the successive administrations are provided as a bolus. A bolus administration is one where the effective amount of the anticoagulant aptamer is provided within a specific time, suitably between 0-30 minutes, 0-20 minutes, 0-10 minutes, 0-5 minutes, or 0-1 minutes.

In some embodiments, the subject is monitored for clotting after administration of the anticoagulant agent and monitoring times are separated by at least the coagulation control time. Suitably the time between administrations may be separated by at least 1 hour, including least 2, 4, 6, 8, 10, 12, or more than 12 hours. The timing and monitoring protocol can be readily determined by the attending clinician or diagnostician, as one skilled in the art, by the use of known techniques and by observing results obtained under analogous circumstances. Laboratory tests used for monitoring adequacy of anticoagulation include, without limitation, activated partial thromboplastin time (aPTT), prothrombin time (PT), activated clotting time (ACT), and rotational thromboelastometry (ROTEM), complete blood count (CBC), hematocrit level, or hemoglobin level amongst others.

In some embodiments, the anticoagulant agent is an aptamer or a composition comprising an aptamer. Aptamers are small, single-stranded oligonucleotides whose linear sequences encode specific three-dimensional structures that allow them to bind to their target proteins or other molecules with high affinity and specificity. Oligonucleotide sequences capable of binding to various molecules with high affinity may be determined by screening large libraries of single stranded oligonucleotides in a combinatorial process, such as through systematic evolution of ligands by exponential enrichment (SELEX). Aptamers fold into a tertiary structure and present an extended conformational surface that is complementary to the surface of its target. Because of the numerous specific interactions along the extended binding interface, aptamers often bind their targets with high affinity, e.g., aptamers may have dissociation constants in the low nanomolar range, and a high degree of target specificity. Additionally, since a large part of the target protein is concealed by aptamer binding, aptamers tend to act as antagonists by blocking protein-protein interactions rather than inhibiting active site activity.

Aptamers may be DNA or RNA molecules and may be single stranded or double stranded. The aptamer may comprise chemically modified nucleic acids, for example in which the sugar and/or phosphate and/or base is chemically modified. Such modifications may improve the stability of the aptamer or make the aptamer more resistant to degradation and may include modification at the 2' position of ribose.

Aptamers may be synthesized by methods which are well known to the skilled person. For example, aptamers may be chemically synthesized, e.g. on a solid support. Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer.

Aptamers can have Kd's in the nM or pM range, e.g. less than one of 500 nM, 100 nM, 50 nM, 10 nM, 1 nM, 500 pM, 100 pM. Aptamers may be useful in virtually any situation in which target binding is required, including use in therapeutic and diagnostic applications, in vitro or in vivo. In vitro diagnostic applications may include use in detecting the presence or absence of a target molecule.

Aptamers according to the present disclosure may be provided in purified or isolated form. Aptamers according to the present disclosure may be formulated as a pharmaceutical composition or medicament.

Suitable aptamers may optionally have a minimum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides.

Suitable aptamers may optionally have a maximum length of one of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Suitable aptamers may optionally have a length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Multifunctional aptamers may be prepared that bind to two or more targets with high affinity and specificity. Multifunctional aptamers may be prepared by varying the length of the stems and/or flexible linker regions between each portion of the aptamer that binds an individual target. Multifunctional aptamers are described in U.S. Pat. No. 9,687,529.

Aptamers can be chemically modified. In some embodiments the aptamer is conjugated to a biocompatible polymer. A biocompatible polymer includes polyalkylene oxides such as without limitation polyethylene glycol (PEG), dextrans, colominic acids or other carbohydrate based polymers, polymers of amino acids, biotin derivatives, polyvinyl alcohol (PVA), polycarboxylates, polyvinylpyrrolidone, polyethylene-co-maleic acid anhydride, polystyrene-co-malic acid anhydride, polyoxazoline, polyacryloylmorpholine, heparin, albumin, celluloses, hydrolysates of chitosan, starches such as hydroxyethyl-starches and hydroxy propyl-starches, glycogen, agaroses and derivatives thereof, guar gum, pullulan, inulin, xanthan gum, carrageenan, pectin, alginic acid hydrolysates, other bio-polymers and any equivalents thereof. Preferred is polyethylene glycol, and still more preferred is methoxypolyethylene glycol (mPEG). Other useful polyalkylene glycol compounds are polypropylene glycols (PPG), polybutylene glycols (PBG), PEG-glycidyl ethers (Epox-PEG), PEG-oxycarbonylimidazole (CDI-PEG), branched polyethylene glycols, linear polyethylene glycols, forked polyethylene glycols and multi-armed or "super branched" polyethylene glycols (star-PEG).

"PEG" and "polyethylene glycol" as used herein are interchangeable and include any water-soluble poly(ethylene oxide). Typically, PEGs for use in accordance with the invention comprise the following structure "—(OCH₂CH₂)ₙ—" where (n) is 2 to 4000. As used herein, PEG also includes "—CH₂CH₂—O(CH₂CH₂O)ₙ—CH₂CH₂—" and "—(OCH₂CH₂)ₙO—," depending upon whether or not the terminal oxygens have been displaced. Throughout the specification and claims, it should be remembered that the term "PEG" includes structures having various terminal or "end capping" groups, such as without limitation a hydroxyl or a C1-20 alkoxy group. The term "PEG" also means a polymer that contains a majority, that is to say, greater than 50%, of —OCH₂CH₂— repeating subunits. With respect to specific forms, the PEG can take any number of a variety of molecular weights, as well as structures or geometries such as branched, linear, forked, and multifunctional.

PEGylation is a process whereby a polyethylene glycol (PEG) is covalently attached to a molecule such as an oligonucleotide.

In some embodiments, the anticoagulant aptamer is conjugated to polyethylene glycol. Such conjugation may reduce renal clearance and increase circulating half-life.

Aptamers also benefit from being rapidly and specifically reversible by administration of a second oligonucleotide composed of a complementary sequence. Through Watson-Crick base-pairing with the aptamer, the antidote oligonucleotide neutralizes the ability of the aptamer to bind its target epitope and rapidly reverses its anticoagulant activity.

An anticoagulant aptamer is an aptamer that can directly inhibit one or more steps in a coagulation pathway. Coagulation is the process by which a blood clot forms to reduce blood loss after damage to a blood vessel. Several components of the coagulation system, including both cellular (e.g. platelets) and protein (e.g. fibrin) components, are involved in blood vessel repair. The role of the cellular and protein components can be categorized as primary hemostasis (the platelet plug) and secondary hemostasis (the coagulation cascade). The coagulation system is classically divided into three pathways: the contact (also known as the intrinsic) pathway, the tissue factor (also known as the extrinsic pathway), and the common pathway. Both the contact pathway and the tissue factor pathway feed into and activate the common pathway.

Hemostasis can either be primary or secondary. Primary hemostasis refers to platelet plug formation, which forms the primary clot. Secondary hemostasis refers to the coagulation cascade, which produces a fibrin mesh to strengthen the platelet plug. Secondary hemostasis occurs simultaneously with primary hemostasis, but generally finishes after it. The coagulation factors circulate as inactive enzyme precursors, which, upon activation, take part in the series of reactions that make up the coagulation cascade. The coagulation factors are generally serine proteases. A summary of the coagulation pathway is shown in FIG. 1A.

The intrinsic pathway (contact activation pathway) occurs during exposure to negatively charged molecules, such as molecules on bacteria and various types of lipids. It begins with formation of the primary complex on a negatively-charged, foreign surface or exposed collagen by high-molecular-weight kininogen (HMWK), prekallikrein, and factor XII (Hageman factor). This initiates a cascade in which factor XII is activated, which then activates factor XI, which activated factor IX, which along with factor VIII activates factor X in the common pathway.

The main role of the extrinsic (tissue factor) pathway is to generate a "thrombin burst," a process by which large amounts of thrombin, the final component that cleaves fibrinogen into fibrin, is released instantly. The extrinsic pathway occurs during tissue damage when damaged cells release tissue factor. Tissue factor acts on factor VII in circulation and feeds into the final step of the common pathway, in which factor X causes thrombin to be created from prothrombin.

In the final common pathway, prothrombin is converted to thrombin. When factor X is activated by either the intrinsic or extrinsic pathways, it activates prothrombin (also called factor II) and converts it into thrombin using factor V. Thrombin then cleaves fibrinogen into fibrin, which forms the mesh that binds to and strengthens the platelet plug, finishing coagulation and thus hemostasis. It also activates more factor V, which later acts as an anticoagulant with inhibitor protein C, and factor XIII, which covalently bonds to fibrin to strengthen its attachment to the platelets.

An anticoagulation strategy that inhibits the contact (intrinsic) coagulation pathway without inhibiting the tissue factor (extrinsic) pathway of coagulation prevents clotting triggered by the ECMO circuit while permitting physiologic coagulation to occur at surgical sites. Such contact coagulation pathway inhibition may be accomplished through the use of the anticoagulant aptamers described herein. In some embodiments, the anticoagulant aptamer inhibits one or more of Factor IX, Factor X, Factor XI, Factor XII, or an activated form thereof. Multifunctional aptamers may target two or more different Factors or activated forms thereof. In other embodiments, multifunctional aptamers may target two or more different sites on the same Factor or activated form thereof. Anticogulant aptamers are described in U.S. Pat. No. 9,687,529.

Anticoagulant aptamers suitable for use in the present invention include, but are not restricted to, aptamers that bind and inhibit FIXa (Rusconi et al, Nature 419:90-94 (2002)) and FXa (Buddai et al, J. Biol. Chem. 285:5212-5223 (2010)), and aptamers that bind prothrombin (factor II, FII) (Layzer and Sullenger, Oligonucleotides 17(1):1-11 (2007); Bompiani and Sullenger, unpublished). The latter aptamer also inhibits the catalytic action of thrombin.

An exemplary FIXa aptamer, designated RNA9.3t, is a 35-base RNA oligonucleotide that inhibits the catalytic cleavage of factor X (FX) by FIXa and by the factor VIIIa (FVIIIa)-FIXa complex known as intrinsic factor Xase (FXase). (9.3T; 5'-AUGGGGAC-UAUACCGCGUAAUGCUGCCUCCCCAU-3' (SEQ ID NO: 1) (See U.S. Pat. No. 7,300,922.) FIXa aptamer also binds factor IX (FIX) and inhibits the cleavage of FIX by factor VIIa (FVIIa) but not by factor XIa (FXIa) (Gopinath et al, Thromb. Haemost. 95:767-771 (2006)). A pegylated 31-base modification of 9.3t, the base sequence of which includes multiple 2'-fluoropyrimidines, may be referred to as DTRI-178.

An antidote for 9.3t or DTRI-178 is a 15-base RNA oligonucleotide the 3' to 5' sequence of which is complementary to the 15-base sequence beginning at the 5' end. That antidote, neutralizes the anti-FIXa activity of 9.3t or DTRI-178.

An exemplary FXa aptamer, designated $RNA_{11F7t}$, is a 37-base RNA oligonucleotide (Buddai et al, J. Biol. Chem. 285:5212-5223 (2010)). (11F7T; 5'-GAGAGCCCCAGCGAGAUAAUACUUGGCCCCG-CUCUU-3' (SEQ ID NO: 2) The base sequence of that aptamer includes multiple 2'-fluoropyrimidines, and its 3' terminal base is an inverted deoxythymidine. $RNA_{11F7t}$ inhibits thrombin formation catalyzed by prothrombinase, the complex of FXa, factor Va (FVa), and calcium ions assembled on a phospholipid surface, by inhibiting the interaction between FXa and FVa (Buddai et al, J. Biol. Chem. 285:5212-5223 (2010)). $RNA_{11F7t}$ binds FX as well as FXa (Buddai et al, J. Biol. Chem. 285:5212-5223 (2010)).

An exemplary prothrombin aptamer, designated R9D-147T, is a 58-base truncation of an 82-base RNA oligonucleotide RNA9D-14, the sequence of which was published in 2007 (Layzer and Sullenger, Oligonucleotides 17(1):1-11 (2007) (R9D-14T7; 5'-GGCGGUCGAUCACACAGUU-CAAACGUAAUAAGCCAAUGUACGAGGCAGACGA-CUCGCC-3' (SEQ ID NO: 3) (see also PCT/US06/36109)). In addition to inhibiting the catalytic activity of thrombin on fibrinogen, this aptamer also binds prothrombin and inhibits its cleavage by FXa. An antidote specific for this aptamer has been synthesized and tested.

An exemplary FIXa aptamer is a ROA. (Nimjee et al, Molecular Therapy 14:408-415 (2006); Dyke et al, Circulation 114: 2490-2497 (2006); Chan et al, Circulation 117: 2865-2874 (2008); Chan et al, Journal of Thrombosis & Haemostasis 6: 789-796 (2008)). The ability of prothrombin aptamer and FXa aptamer to prolong the prothrombin time, the partial thromboplastin time, and the thromboelastographic lag time of whole blood within minutes following the addition of either of those aptamers strongly suggests that both of those aptamers, like FIXa aptamer, will also be in vivo ROAs.

An exemplary anticoagulant aptamer for use in the methods described herein is DTRI-178. DTRI-178 is a 35-nucleotide RNA anticoagulant aptamer conjugated to polyethylene glycol that increases its half-life in circulation. This aptamer that inhibits the formation of intrinsic tenase by binding to a factor IXa noncatalytic exosite. Using a piglet model of pediatric venoarterial (VA) ECMO, we compared thromboprevention and blood loss using a single dose of DTRI-178 monotherapy versus UFH infusion (standard of care). In each of five experiments, we subjected two litter-matched piglets, one anticoagulated with DTRI-178 and the other with UFH, to simultaneous 12-hour periods of VA ECMO. Each anticoagulant achieved satisfactory and comparable thromboprotection. However, piglets anticoagulated with UFH had increased surgical site bleeding and required significantly greater blood transfusion volumes than piglets anticoagulated with DTRI-178. Finally, whole blood samples from three patients on venovenous (VV) ECMO for severe COVID-19 pneumonia and from two healthy donors were treated with DTRI-178. The anticoagulation effects of DTRI-178 on COVID-19 patient blood while on ECMO as measured by conventional and viscoelastic hemostatic tests (ROTEM) were comparable to that from healthy donors, suggesting efficacy in this patient population. Our results indicate that DTRI-178, an aptamer against factor IXa, may be feasible, safer, and result in fewer transfusions and clinical bleeding events in ECMO. DTRI-178 may also serve as a suitable anticoagulant for COVID-19 patients who undergo ECMO and provide hemostatic benefits in this population as well.

FIXa is the enzymatic component of intrinsic tenase, the final procoagulant enzyme complex in the contact (intrinsic) coagulation pathway. The anticoagulant aptamer 9.3t is a 35-base RNA anticoagulant aptamer that binds a human FIXa exosite in a manner that inhibits FIXa from binding its cofactor, FVIIIa, thereby inhibiting the formation of the intrinsic tenase. This molecule has also been shown to bind and inhibit porcine FIXa, and has been used to achieve anticoagulation in a piglet model of cardiopulmonary bypass. Clinical investigations of DTRI-178, a PEGylated formulation of 9.3t previously named RB006, showed that it achieved satisfactory anticoagulation in patients who were undergoing percutaneous coronary intervention. Therefore, DTRI-178 presents an attractive and highly specific means of inhibiting the final step of the contact activation pathway while allowing coagulation to occur via the tissue factor (TF, extrinsic) coagulation pathway.

In some embodiments of the invention, aptamer may comprise or consist essentially of an oligonucleotide sequence having at least 50%, 60%, 70%, 80%, 85%, 90%, 91%, 92%, 93%, 94%, 95%, 96%, 97%, 98%, 99%, or 100% sequence identity to any one of SEQ ID NOS: 1-3. The terms "sequence identity," "percent identity," and "% identity" refer to the percentage of base matches between at least two nucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Sequence identity for a nucleotide sequence may be determined as understood in the art. (See, e.g., U.S. Pat. No. 7,396,664).

Assessing the efficacy of FIXa inhibition for thromboprevention during ECMO requires in vivo modeling with high clinical fidelity. Pigs (*Sus scrofa*) are commonly used as large animal models of human disease due to their similar cardiopulmonary physiology, cardiovascular anatomy, and hemostatic systems. Young pigs and piglets have been utilized as models of pediatric ECMO in order to study ECMO-induced ischemic and inflammatory changes, and in a model of cardiopulmonary bypass to compare the efficacy of anticoagulants. Conventional coagulation parameters and individual factor activities in swine have been described in detail but generally, pigs have higher activities of the same intrinsic coagulation factors established in humans (i.e., IX, XI, and XII). This high degree of conservation is inferred from both porcine enzymatic activity in assays using human substrates and structural analysis of clots ex vivo; as well as from overall interspecies amino acid sequence homology. Given the similarities between human and pig cardiovascular and coagulation systems, as well as prior establishment of models for extracorporeal support in piglets, a porcine model was selected to examine the effects of selective FIXa inhibition during VA ECMO.

The use of ECMO has steadily increased worldwide. Despite other advances in the field and well-established risks of hemorrhage and HIT, UFH infusion has remained the standard of care since the inception of ECMO in the 1970s. The present Examples demonstrate that animals anticoagulated with either an anti-FIXa aptamer or UFH have comparable thromboprevention, but that piglets anticoagulated with the aptamer have significantly better hemostasis.

Although FIX is activated to FIXa during TF-FVIIa complex-mediated coagulation, it is not required for FXa generation in the presence of TF. Therefore, thrombin can be generated with subsequent platelet aggregation and fibrin polymerization by TF-FVIIa complexes in the absence of FIXa. More recent studies have also described activation of FIX in a non-canonical pathway by the contact activation protease kallikrein, suggesting that foreign surfaces may be a very proximal stimulus for FIXa generation via kallikrein and independent of other mechanisms. Using the whole blood ROTEM assay, the Examples show that DTRI-178 permits TF pathway-mediated FX activation, thereby preserving normal EXTEM parameters and hemostatic capacity in response to tissue trauma (i.e., surgical manipulation for the ECMO cannulation procedure). Simultaneously, DTRI-178 prevented undesired clot formation in and on the synthetic oxygenator.

These findings are a potentially significant advance in the development of a more rational systemic anticoagulation strategy for ECMO patients, and might reduce bleeding, decrease cost, and improve survival. These findings are of particular interest in the treatment of patients with pre-existing coagulopathies who may be at the highest risk of hemorrhage and/or thrombosis. Patients undergoing a prolonged resuscitation, premature and early-term infants with increased intraventricular hemorrhage risk, those with disseminated intravascular coagulation, and those with severe COVID-19 pneumonia might stand to benefit most from more selective approaches to anticoagulation and improvement in hemostasis. Additionally, the global COVID-19 pandemic highlights the potential for unprecedented and sudden increases in the need for ECMO, as well as attendant needs for safer anticoagulation in circumstances where hemostatic anomalies are present.

DTRI-178's ability to anticoagulate blood from a donor with severe COVID-19 pneumonia requiring ECMO, ROTEM and ACT-LR findings suggested similar anticoagulation efficacy to that obtained in healthy donor blood. The clot firmness and extrinsic pathway were preserved in a manner similar to that seen in our piglet model. Given the scale of the ongoing public health crisis associated with this infection and its propensity for devastating thrombotic and hemorrhagic events, DTRI-178 is an exciting and novel anticoagulant for this vulnerable population.

Our findings have significant implications not only for ECMO, but also for other applications in which blood-foreign surface contact necessitates ongoing anticoagulation. Ventricular assist devices (VADs) for heart failure, for example, typically utilize a centrifugal pump very similar to most ECMO systems. Patients with VADs routinely receive oral vitamin K antagonists, which carry considerable hemorrhagic risk and associated complications, including mortality.

Given the considerable risks of UFH, there has been recent interest in development of alternative anticoagulation strategies for a myriad of applications in which UFH is typically the standard of care, including ECMO.

The Examples demonstrate a strategy that targets a critical component of the intrinsic tenase complex that is dispensable for TF-FVIIa complex-mediated coagulation. The Examples demonstrate very favorable hemostasis in our model using FIXa inhibition while maintaining thromboprevention comparable to that achieved with UFH. The basis for this relative preservation of hemostasis may be multifactorial and complex. 9.3t inhibits formation of intrinsic tenase. As intrinsic tenase activates FX orders of magnitude faster than does free FIXa, that effect alone likely provides potent anticoagulation. This is the basis for aPTT prolongation and likely the mechanism for thromboprevention during ECMO. It is believed that 9.3t disrupted the formation of pre-formed intrinsic tenase by binding FIXa; i.e., by "pulling" FIXa away from FVIIIa. In a separate report, Gopinath et al demonstrated that 9.3t, by binding FIX, also inhibited TF:FVIIa-mediated FIXa activation, but not FXIa-catalyzed cleavage of FIX.

The compounds utilized in the methods disclosed herein may be formulated as pharmaceutical compositions that include: (a) a therapeutically effective amount of one or more anticoagulant agents or anticoagulant apatmers; and (b) one or more pharmaceutically acceptable carriers, excipients, or diluents. The compounds utilized in the methods disclosed herein may be formulated in any pharmaceutically acceptable dosage form can be utilized. The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. The compounds utilized in the methods disclosed herein may be administered in conventional dosage forms prepared by combining the active ingredient with standard pharmaceutical carriers or diluents according to conventional procedures well known in the art. In some embodiments, the anticoagulant agent is administered intravenously or other acceptable administration route.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Methods

Ten litter-matched, approximately two-week old Yorkshire farm piglets, 4.5 to 5.5 kg, were randomized to control (UFH) or aptamer (DTRI-178) study groups. Ten juvenile Yorkshire pigs (3-4 months of age, 30-55 kg) were utilized for circuit priming and blood transfusion. All piglets and donor animals were confirmed to be blood type O with EldonCard (Eldon Biologicals, Gentofte, Denmark) kits as previously described (40).

DTRI-178 Anticoagulation

The in vivo and in vitro activities of DTRI-178 in human blood have been previously described (Tanaka K A, Szlam F, Rusconi C P, Levy J H. In-vitro evaluation of anti-factor IXa aptamer on thrombin generation, clotting time, and viscoelastometry. Thromb Haemost. 2009; 101(5):827-33; Dyke C K, Steinhubl S R, Kleiman N S, Cannon R O, Aberle L G, Lin M, et al. First-in-human experience of an antidote-controlled anticoagulant using RNA aptamer technology: a phase 1a pharmacodynamic evaluation of a drug-antidote pair for the controlled regulation of factor IXa activity. Circulation. 2006; 114(23):2490-7). In order to confirm species specificity and estimate dosing in porcine models, normal plasma was obtained from 10 healthy adult pigs, pooled, and subjected to aPTT tests with graded dilutions of DTRI-178. Briefly, 10-fold dilutions of DTRI-178 were added to pooled normal porcine plasma for final reaction mixture concentrations of $5\times10^{-3}$ µM to 5 µM in 20 mM HEPES buffer, pH 7.4. The plasma-aptamer mixture was incubated for 5 minutes at 37° C. before addition of the silica-based SynthasIL aPTT activation reagent (Instrumentation Laboratory). After 2 minutes of incubation with the activation reagent, calcium chloride 0.2 M was added to commence coagulation (Instrumentation Laboratory), and a BBL fibrometer (BD, Franklin Lakes, New Jersey) was used to measure the time until coagulation began. All tests were performed in triplicate, and the aptamer concentration at which the aPTT was doubled was selected for further experimentation in vivo.

Donor Blood Collection Procedures

After overnight fasting, two donor animals were sedated with intramuscular ketamine (22 mg/kg) and acepromazine (1.1 mg/kg), and then anesthetized with isoflurane (1-5%), intubated and mechanically ventilated. Following infiltration with 1% bupivacaine, the right carotid artery was exposed and cannulated for whole blood collection. The first 5 mL of blood was discarded, and then donor collection bags containing sterile anticoagulant-citrate-dextrose A (ACD-A, Fenwal Inc., Lake Zurich, Illinois) were filled with donor blood in a 1:8 ratio. When sluggish flow was encountered at the end of the collection or in the case of incompletely filled bags, the blood was discarded. After exsanguination, donor animals were sacrificed humanely under deep anesthesia with approved methods, and the piglet ECMO cannulation procedure commenced immediately.

Donor blood was stored at 4° C., and individual bags were introduced into each of the two ECMO circuits in each experiment in the same order (in order to maintain similar donor-recipient dynamics). Blood was transfused through the heated ECMO circuit to prevent hypothermia. All blood was utilized within 24 hr of collection.

Piglet Cannulation Procedures and ECMO Circuit Description

After 8 hours of fasting, two litter-matched piglets were sedated with isoflurane (1-5%) and IV propofol infusion (4-10 mg/kg/hr). After infiltration of bupivacaine, a femoral arterial catheter and suprapubic urinary bladder catheter were placed for monitoring. The first piglet's assignment (UFH versus aptamer) was alternated for each of the five study days. The right common carotid artery and external jugular vein were exposed with blunt and sharp dissection, and both vessels were controlled with monofilament suture. Immediately prior to carotid ligation and arteriotomy, an anticoagulant bolus (heparin for goal ACT 180-200 s or target plasma aptamer concentration 0.50 μm) was administered. Finally, the common carotid artery and external jugular vein were cannulated under direct vision with 8 Fr venous and 8 Fr arterial cannulae (Biomedicus Medtronic, Minneapolis, Minnesota). The arterial and venous cannulae were advanced 2-3 and 7 cm, respectively, and their tip positions were confirmed at necropsy to be in the transverse arch of the aorta and cavoatrial junction, respectively.

Figure 1B:
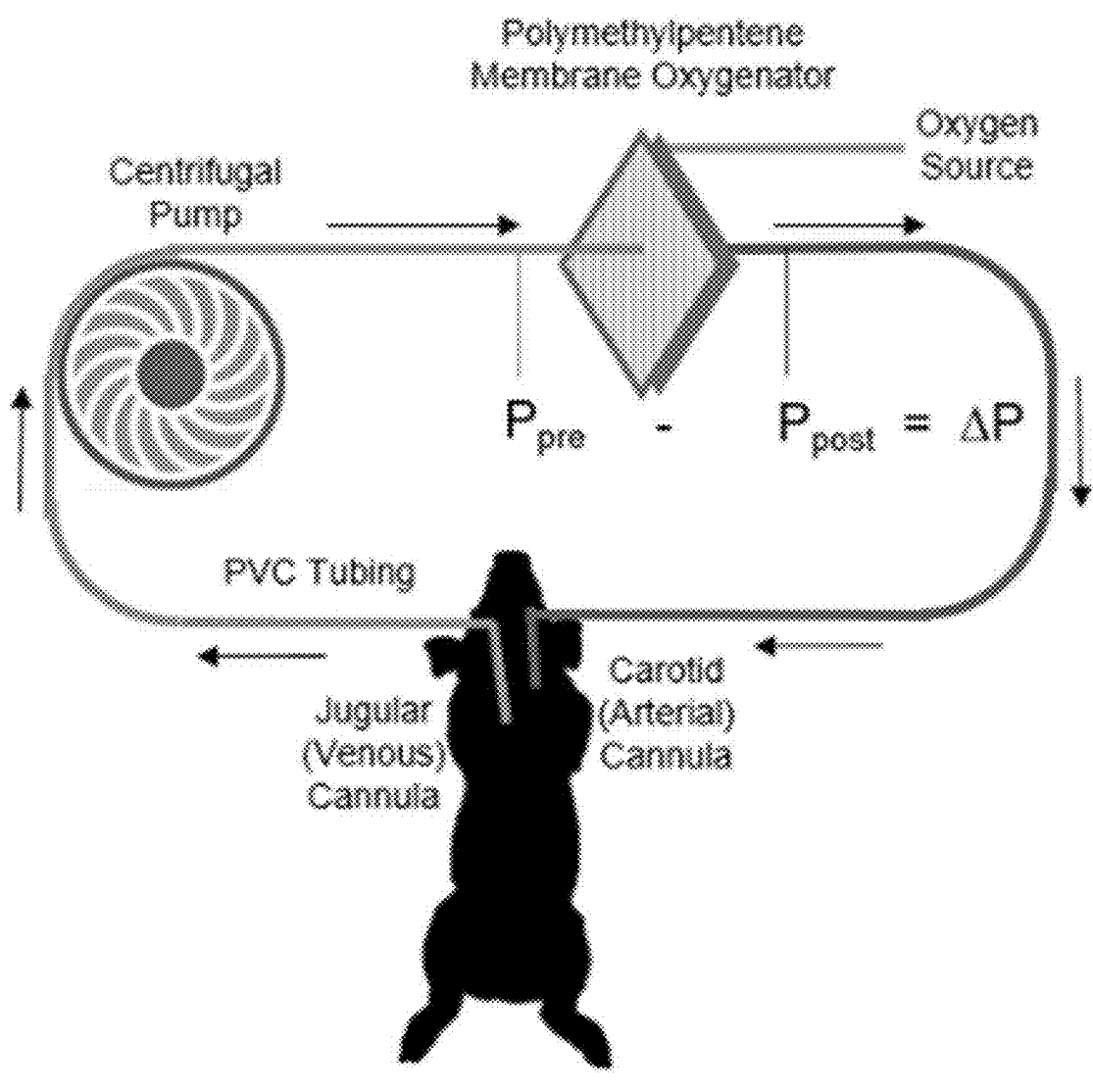
FIG. 1B shows a schematic of extracorporeal membrane oxygenation (ECMO) circuit.

Simultaneously, the ECMO circuit was prepared in a manner consistent with our clinical practice (FIG. 1B). Venous blood is withdrawn from the superior cavoatrial junction via an 8 Fr cannula. A centrifugal pump (artificial heart) pumps blood through a polymethylpentene membrane oxygenator (artificial lung), where gas exchange and warming occurs. Arterialized blood is then returned via the arterial cannula terminating in the arch of the aorta. Resistance to flow across the membrane oxygenator is estimated by transduction of hydrostatic pressure immediately prior to ($P_{pre}$) and after ($P_{post}$) the oxygenator.

The circuit employed uncoated polyvinylchloride tubing and a centrifugal magnetic levitation pump from a commercially available perfusion pack (Custom Revolution Pump Base Pack and Tubing Pack, Sorin Group Liva Nova, London, United Kingdom). An adult membrane oxygenator was used (Quadrox-iD, Maquet Getinge Group, Wayne, New Jersey). The circuit was clear-primed in anticipation of cannulation with the calcium-free balanced saline-containing crystalloid Plasalyte-A (Baxter International, Deerfield, Illinois). Immediately prior to commencing ECMO, the circuit was primed with whole citrated donor blood (~450 mL), followed by anticoagulation (300 U heparin or target plasma aptamer concentration 0.50 μm), recalcification with 500 mg $CaCl_2$, and 3-5 mEq sodium bicarbonate for a target pH of 7.4.

ECMO Settings, Monitoring, and Lab Draws

The target ECMO flow was 120 mL/kg/min (range: 80-160 mL/kg/min) and the pump speed was the dependent variable. The sweep gas was initially set to ⅟₃₂ L/min of flow and titrated to achieve a $PaCO_2$ 40-60 mmHg. The pressure gradient across the membrane oxygenator ($P_{pre}-P_{post}=\Delta P$) was calculated as a real-time surrogate of oxygenator clot burden. All settings were recorded hourly. Vital signs including rectal temperature, heart rate, SpO2, respiratory rate, end-tidal $CO_2$, and femoral arterial blood pressure were recorded every 15 minutes for the first four hours and then every 30 minutes thereafter.

Piglets underwent arterial blood gas (ABG) sampling via femoral catheter every hour using a GEM Premier 3000 analyzer with fresh whole blood (Instrumentation Laboratory, Bedford, Massachusetts). Hematocrit was measured every hour and a 10 mL/kg transfusion was delivered if ABG hematocrit was <21%. In order to exclude variability incurred during cannulation or at baseline, only transfusions after 4 hr were compared. Based on previously established ECMO modeling in piglets as well as clinical guidelines for humans, an UFH anticoagulation target using ACT 180-220 s was established a priori (33, 43). Hourly MAX-ACT with an Actalyte Mini II analyzer (Helena Laboratories, Beaumont, Texas) was performed with fresh whole blood to monitor heparin anticoagulation hourly. Heparin infusion rate adjustments were made after any MAX-ACT value outside of the 180-220 s range. The MAX-ACT was repeated 5 minutes after subtherapeutic (<180 s) or very supratherapeutic (>250 s) readings until a therapeutic range reading was obtained. For aptamer-treated piglets, low-range ACT (ACT-LR, Instrumentation Laboratory Bedford, Massachusetts) was performed hourly with a HemoChron Jr Signature analyzer (Instrumentation Laboratory) designed to monitor patients receiving less potent anticoagulation.

Finally, rotational thromboelastometry (ROTEM) tests of the extrinsic, intrinsic, and fibrin-only (EXTEM, HEPTEM or INTEM, and FIBTEM; respectively) coagulation pathways were performed at baseline, after anticoagulation but pre-ECMO, 5 minutes after starting ECMO, and then at 4, 8, and 12 hours after starting ECMO (Instrumentation Laboratory). In order to account for the effects of heparin (which arrests INTEM intrinsic coagulation entirely at the concentrations utilized in this experiment) and probe for underlying coagulopathy, all heparin-containing specimens were pretreated with heparinase as per the manufacturer HEPTEM protocol. Citrated whole blood and commercially available reagents from Instrumentation Laboratory were used for ROTEM testing on a ROTEM delta analyzer according to manufacturer instructions, and reactions were allowed to proceed for at least 30 minutes.

Additional laboratory testing included complete blood count (CBC) obtained with an automated hematology analyzer (Sysmex Model KX-21N, Lincolnshire, Illinois) at 0, 4, 8, and 12 hours; and quantitative fibrinogen levels (IDEXX BioAnalytics, North Grafton, Massachusetts) at 0, 4, and 12 hours.

Membrane Oxygenator Analyses

At the completion of each run, membrane oxygenators were gently rinsed with isotonic normal saline to remove blood, and then the face of each oxygenator was photographed for clot quantification. Oxygenators were then processed for scanning electron microscopy (SEM). Briefly, a 3×3 cm section of the outermost superficial layer of the oxygenator membrane and a similar-sized section of deep interior layer were cut and then dehydrated in graded series of aqueous ethanol (50%, 70%, 90% and then three times in 100%). A final dehydration step was completed in hexamethyldisilazane (EM Sciences, Hatfield, Pennsylvania) before specimens were placed in a dehydration chamber overnight. Samples were sputter-coated with gold in a Desk V unit (Denton Vacuum, Moorestown, New Jersey). Finally, 1×1 cm sections from both shallow and deep portions of the oxygenator were mounted onto aluminum stubs. Ten random images were acquired from both depths on each of six oxygenators (3 UFH, 3 aptamer) at 200,000× magnification using an Apreo S scanning electron microscope (ThermoFisher Scientific, Hillsboro, Oregon).

For photography analysis and comparison, lossless TIF photographs of all 10 oxygenators were analyzed in Fiji by two blinded authors (44). Both authors quantified the number of macroscopic clots as well as the overall percent of the oxygenator face that was clotted. The number of clots and percent of oxygenator face clotted for both experimental groups were ultimately expressed as the mean and standard error of the mean of the duplicate means calculated for each oxygenator.

For SEM analysis, all 20 images (10 superficial, 10 deep) for each of the three oxygenators per study group were analyzed for combined fibrin and cellular clot burden by the same blinded authors. In a manner similar to that described above for photographs, Fiji was used to count all clots ≥5 μM in any dimension, and then to estimate the percent area clotted.

DTRI-178 in COVID-19 and ECMO

As a pilot investigation into the efficacy of DTRI-178 as an anticoagulant in the context of severe COVID-19 pneumonia requiring VV ECMO, we used ROTEM and ACT-LR tests as described above to compare whole blood from three COVID-19 VV ECMO patients with that from two healthy donors. One sample of citrated whole blood was requested from each critically ill COVID-19 patient on VV ECMO enrolled in the COVID-19 ICU Biorepository. Citrated fresh whole blood was treated either with buffer or with DTRI-178 for a final target plasma concentration of 0.5 µM to match the animal study dose. Buffer- and DTRI-178-treated specimens were then analyzed with ROTEM (HEPTEM, EXTEM, FIBTEM, and INTEM as above) or ACT-LR immediately after recalcification. The blood sample from one of the healthy donors was heparinized to a calculated concentration of 0.5 U/mL in order to estimate therapeutic heparin concentrations used in practice and match that of ⅔ COVID-19 patients, who were heparinized for ECMO. All study activities were reviewed and approved by the Duke University Institutional Review Board (Pro00101196, 0063122, and 00105315). Basic clinical variables were also recorded and described.

Statistical Analysis

Data were analyzed and graphed using Graphpad Prism 8 (Graphpad Software, San Diego, California). Continuous data were described using the mean and standard error of the mean. Point comparisons of continuous variables between study groups (i.e., weight) were made using a two-tailed t-test. Trends of continuous variables over time (i.e., ECMO flows and ΔP) were compared with simple linear regression analysis. The slope of each regression line was tested for deviance from zero. For all tests, $p<0.05$ was interpreted as statistically significant. No correction was made for multiple comparisons.

Results

UFH and DTRI-178 Both Maintain Circuit Patency in Piglet ECMO

Figures 9A, 9B:
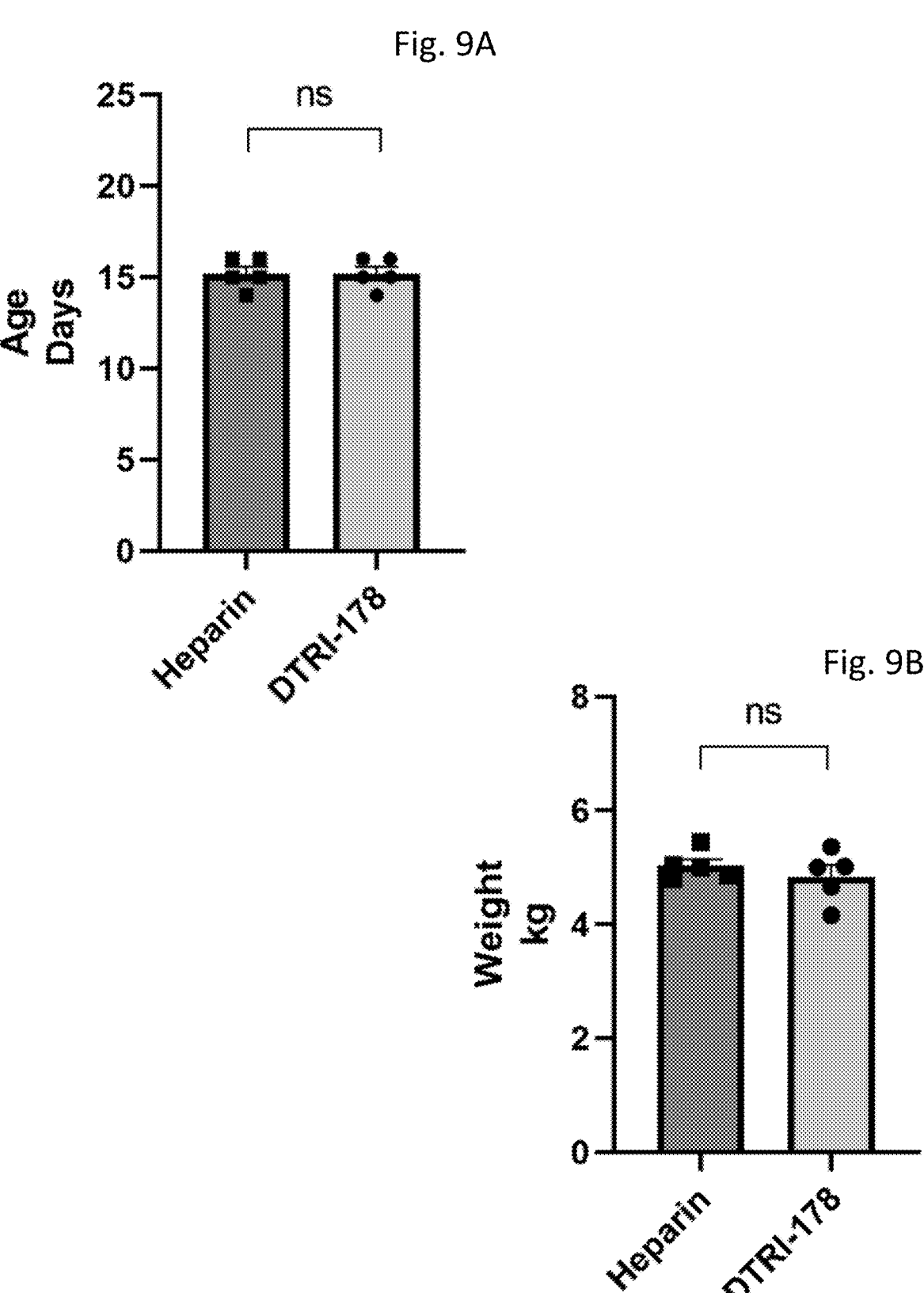
FIGS. 9A-9B shows piglet (FIG. 9A) age and (FIG. 9B) weight of piglets on day of ECMO.

Five pairs of piglets (5 UFH, 5 aptamer) were cannulated for VA ECMO and supported through the study end-point of 12 hours. Each pair came from a single litter and were therefore identical in age (mean=15.2 days, FIGS. 9A-9B). The mean weight was 5.03 kg for the UFH group and 4.84 kg for the aptamer group (p=0.4407).

Figure 2A:
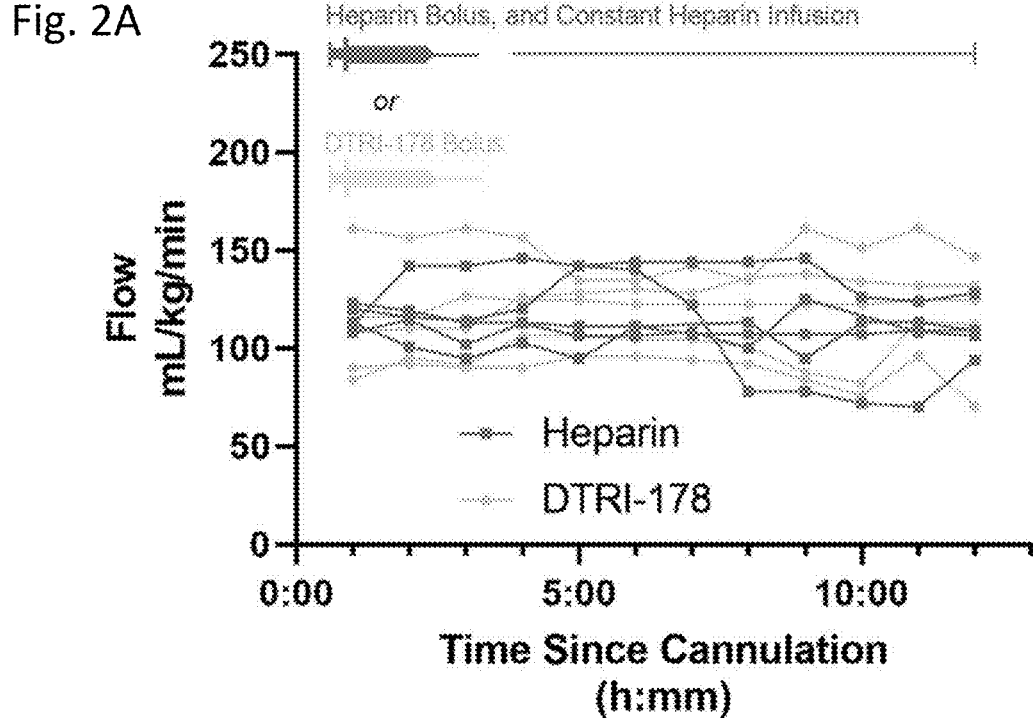
FIGS. 2A-2B show blood flow and transmembrane oxygenator pressures through the extracorporeal membrane oxygenation (ECMO) circuit over time.
Figure 2B:
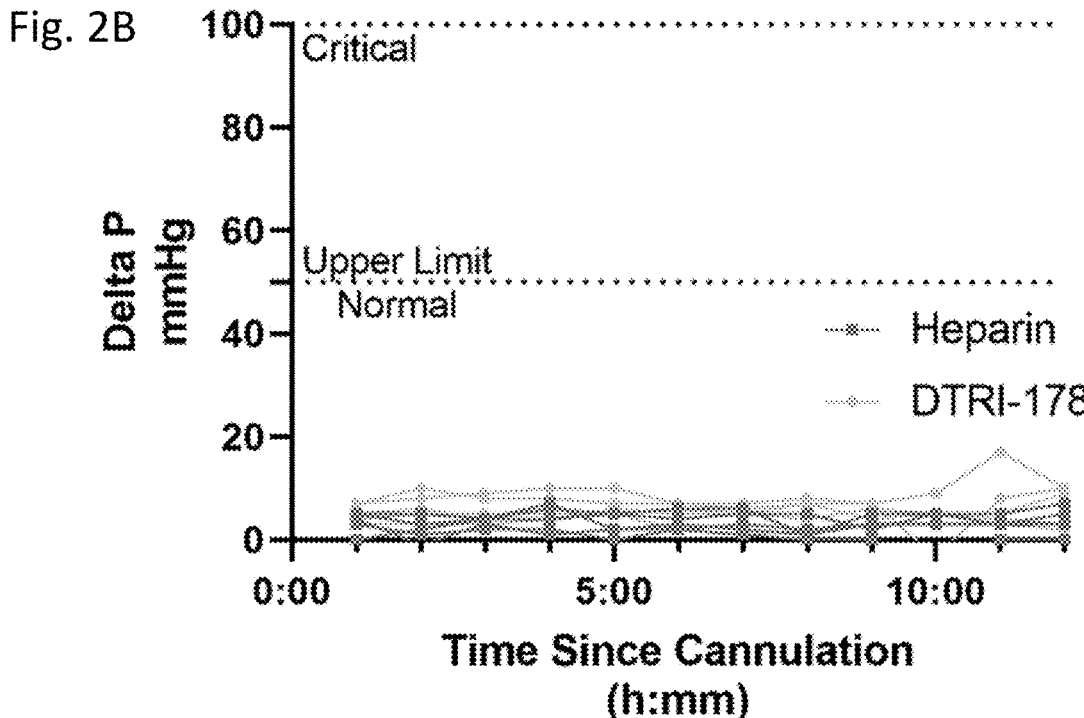
Figure 4C:
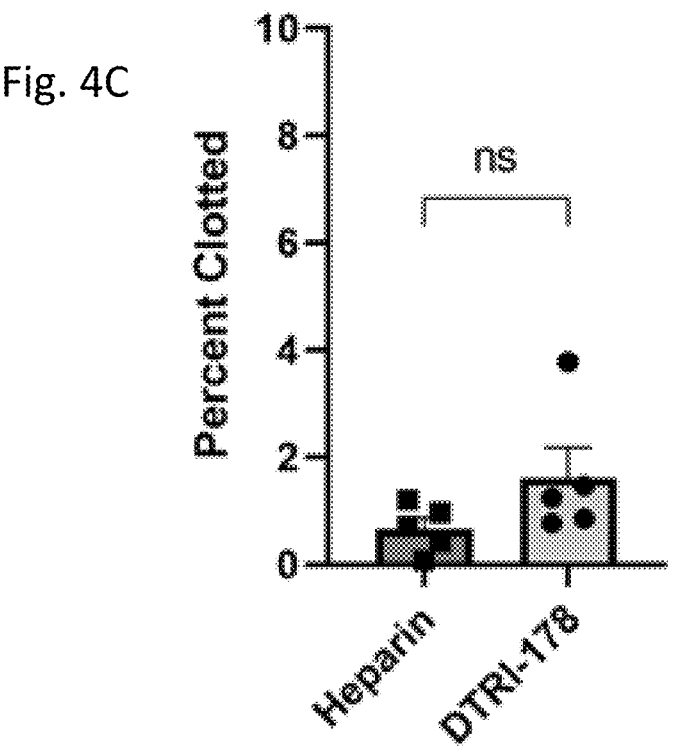
Figure 4F:
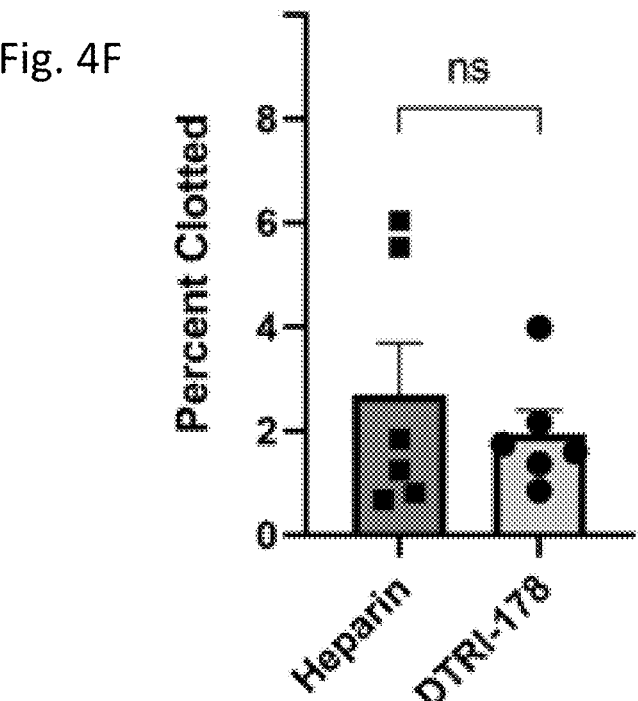

All animals achieved and maintained good ECMO flows throughout the experiment (FIGS. 2A-2B). Mean flows ranged from 100-140 mL/kg/min and were stable throughout the procedure for both groups. There were no significant differences in the flow trends over time between the study groups. The estimated slope of the best fit line for the heparin group was −1.121 (probability of being non-zero, p=0.0986) and was 0.4611 for the DTRI-178 group (probability of being non-zero, p=0.6308).

Figure 10A:
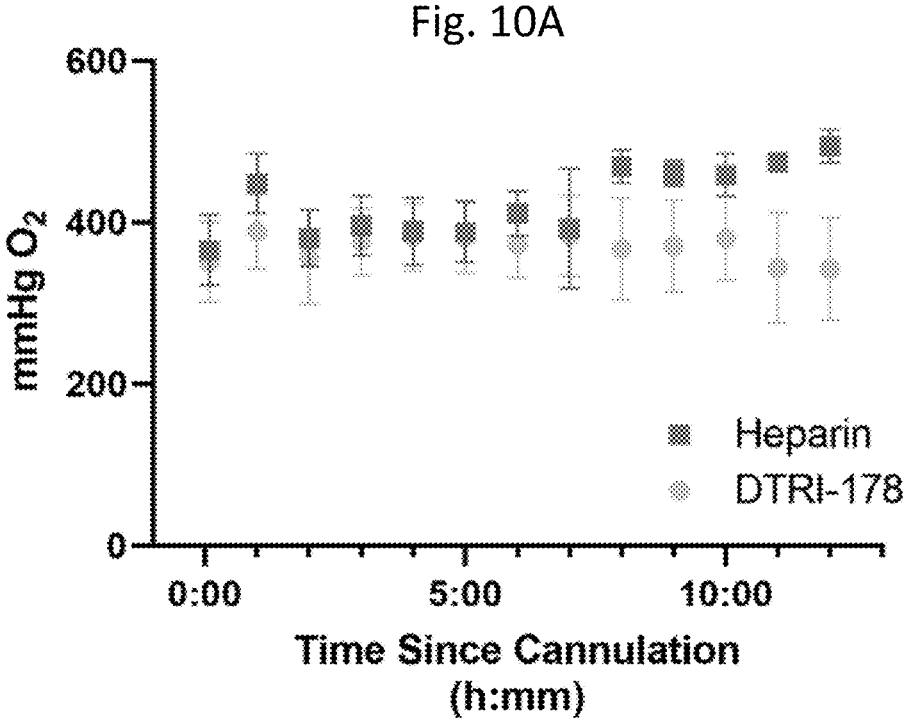
FIGS. 10A-10B show mean partial pressures of arterial blood oxygen (PaO$_2$) and carbon dioxide (PaCO$_2$). Samples taken hourly from indwelling femoral arterial catheter; each point is the mean of five time points±standard error of the mean.
Figure 10B:
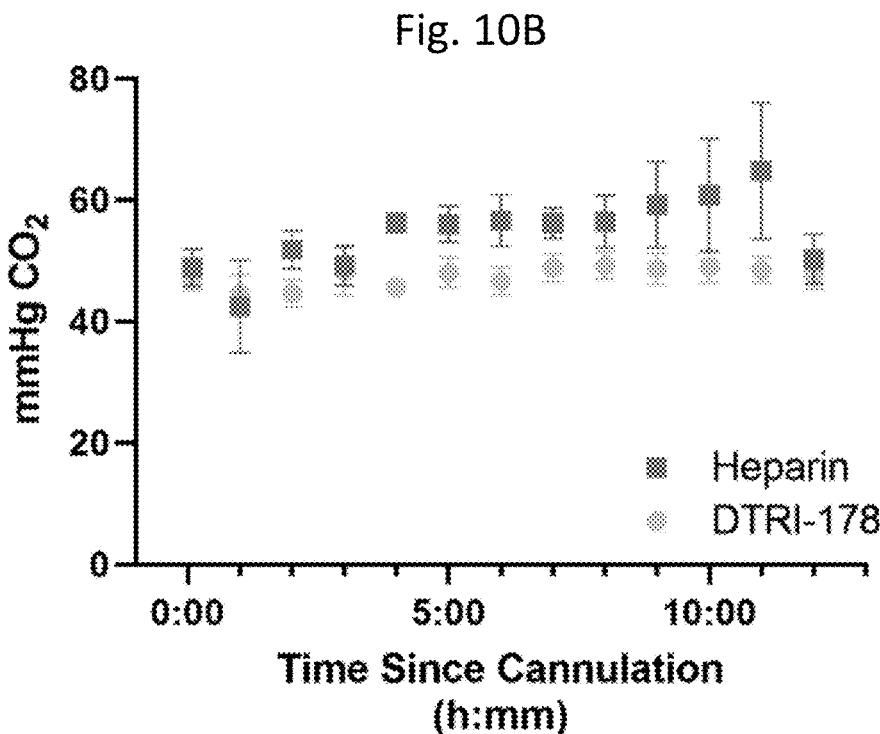

Transmembrane oxygenator pressure gradient (ΔP), a measure of resistance to flow through the oxygenator and surrogate for oxygenator clot burden, was negligible for both groups at all but one time point in every experiment. There was one outlying 17 mmHg measurement at 11 hr from an aptamer-treated animal, which normalized by the next hour's data collection point (mean ΔP for all other measurements in all animals in all experiments ≤10 mmHg). Oxygenation and decarbonation were adequate in both experimental groups throughout each run, although $PaCO_2$ tended to increase throughout the run in the case of heparinized animals (FIGS. 10A-10B).

Hemostasis is Superior with Aptamer Compared to Heparin

Animals in the UFH group required significantly more blood transfusions in order to address hematocrit instability (FIGS. 3A-3E, 47.4 mL/kg versus 3.9 mL/kg, p=0.0020). Furthermore, 2/5 animals in the aptamer group did not require any transfusions in order to maintain hematocrit stability despite repeated blood draws for laboratory studies and monitoring, while all animals in the UFH group required repeated transfusions. This corresponded with slow but persistent hemorrhage from cannulation and suprapubic bladder/femoral arterial catheterization sites for the duration of the run in 5/5 UFH animals. In contrast, 3/5 aptamer-treated animals had immediate hemostasis after the initial procedures, with the remainder achieving delayed hemostasis by the end of the experiment.

Aptamer and Heparin Provide Equivalent Thromboprevention

After rinsing away residual blood with crystalloid, high-resolution photographs of all 5 oxygenators from each treatment group were examined to compare macroscopic clot burden (FIGS. 4A-4F). In agreement with negligible ΔP throughout each run, clot burden was overall low in both groups. There was no significant difference in the mean percentage of the oxygenator face occupied by clot on photography (0.67% for UFH versus 1.62% for aptamer, p=0.1460).

Ten regions from each of two layers (superficial, deep) from each of three oxygenators in each treatment group (UFH, DTRI-178) were analyzed with SEM. Blinded manual counting revealed no significant difference in the mean percent of area clotted among oxygenators from animals treated with UFH (2.69%) versus aptamer-treated animals (1.95%, p=0.6686) utilizing SEM.

Aptamer Anticoagulation is Quantifiable and Durable

Figure 5:
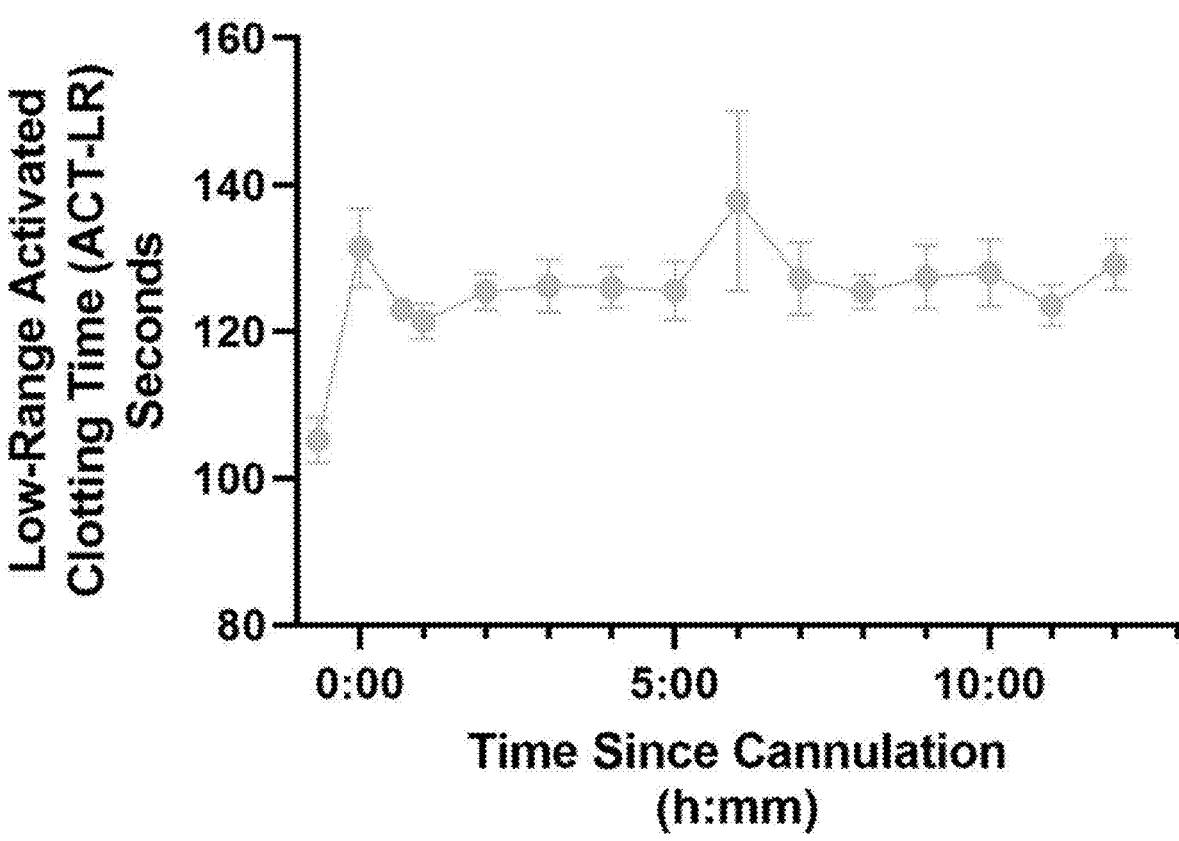
FIG. 5 shows low-range activated clotting time (ACT-LR) in DTRI-178-treated animals. The first point (before time 0) is the baseline reading prior to DTRI-178 administration, the second point (at time 0) is immediately prior to starting ECMO, and the third point is immediately after commencing extracorporeal circulation.
Figure 6A:
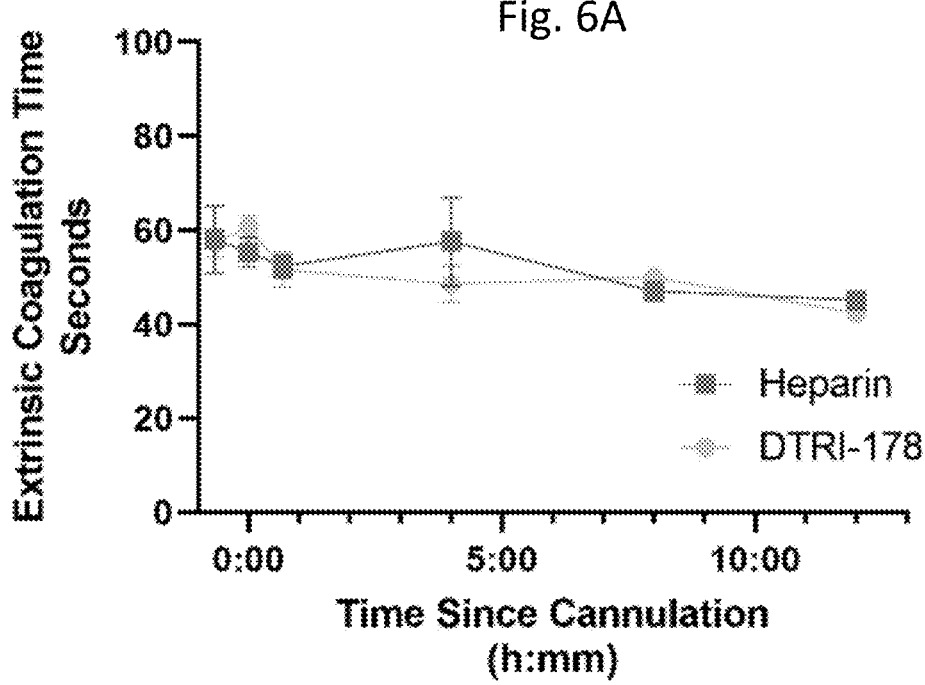
FIGS. 6A-6E show rotational thromboelastometry (ROTEM) analyses of the extrinsic (EXTEM), intrinsic (INTEM or HEPTEM), and acellular fibrin-only (FIBTEM) pathways of coagulation. The first point (before time 0) is the baseline reading prior to DTRI-178 administration, the second point (at time 0) is immediately prior to starting ECMO, and the third point is immediately after commencing extracorporeal circulation.
Figure 6B:
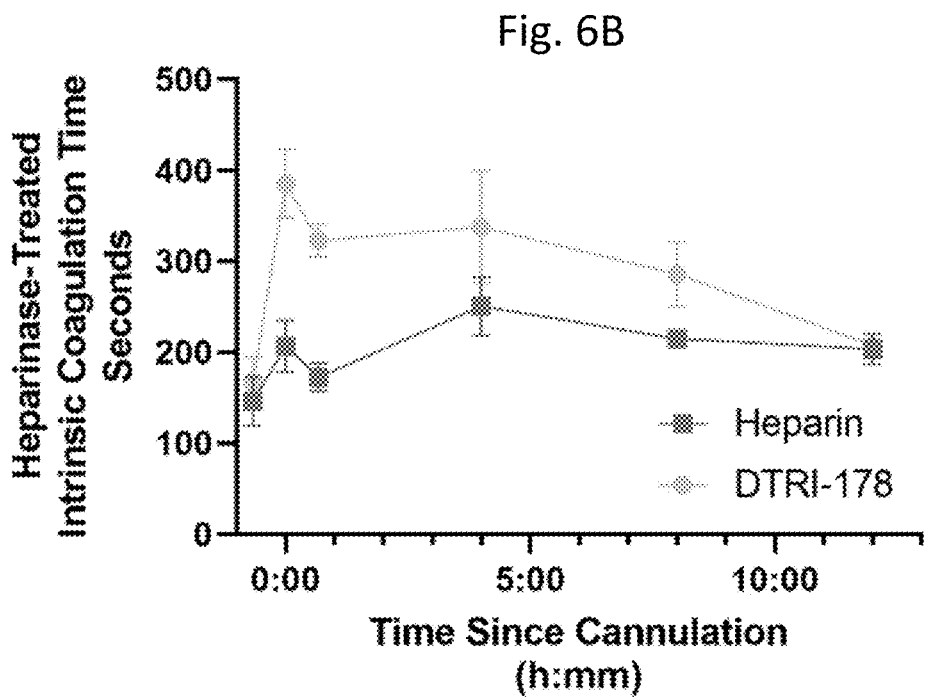
Figure 6C:
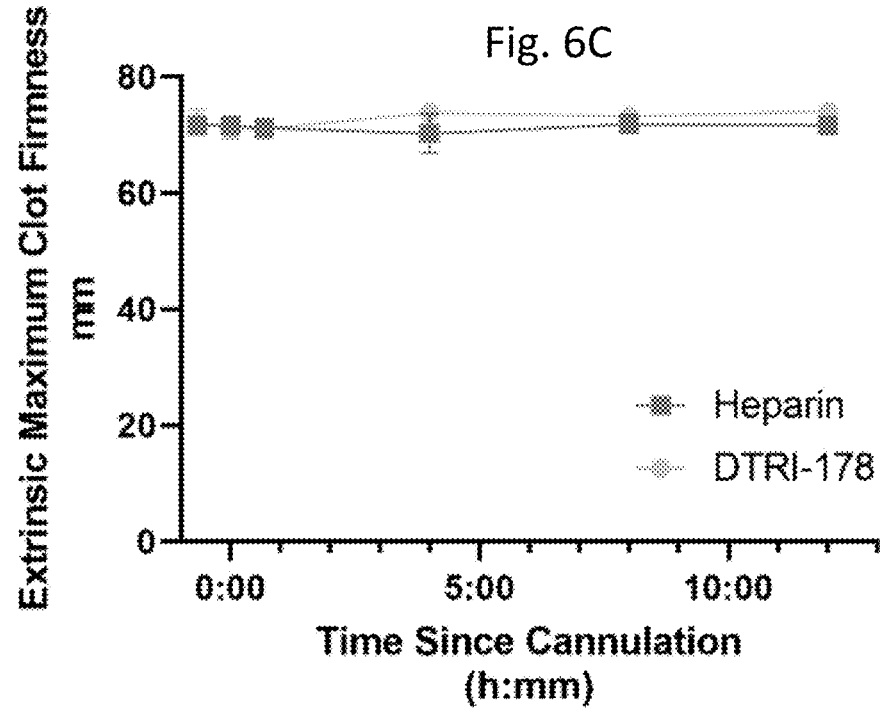
Figure 6D:
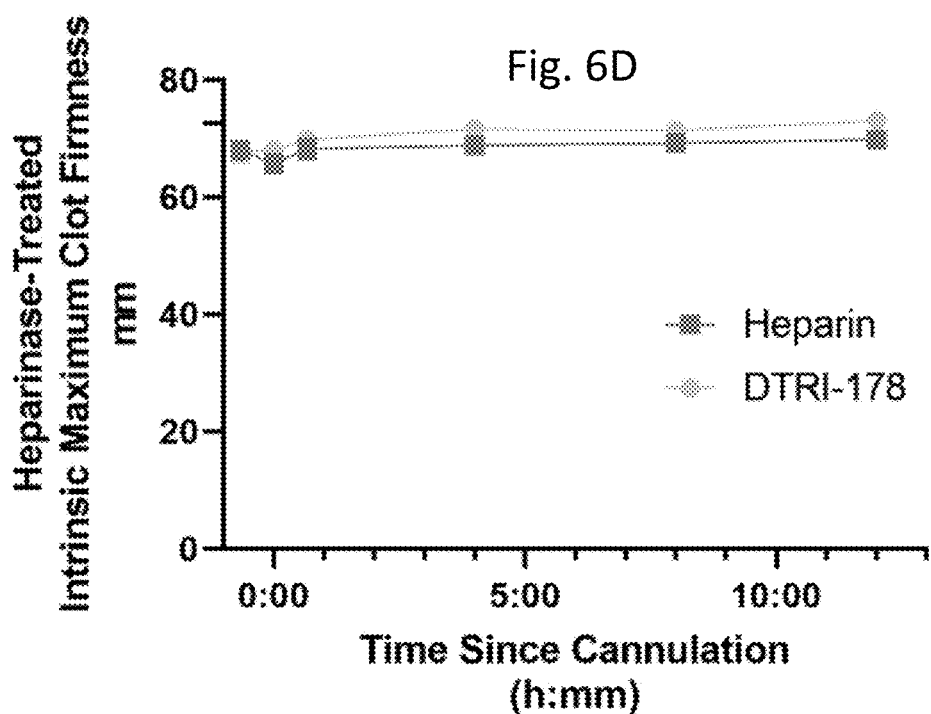
Figure 6E:
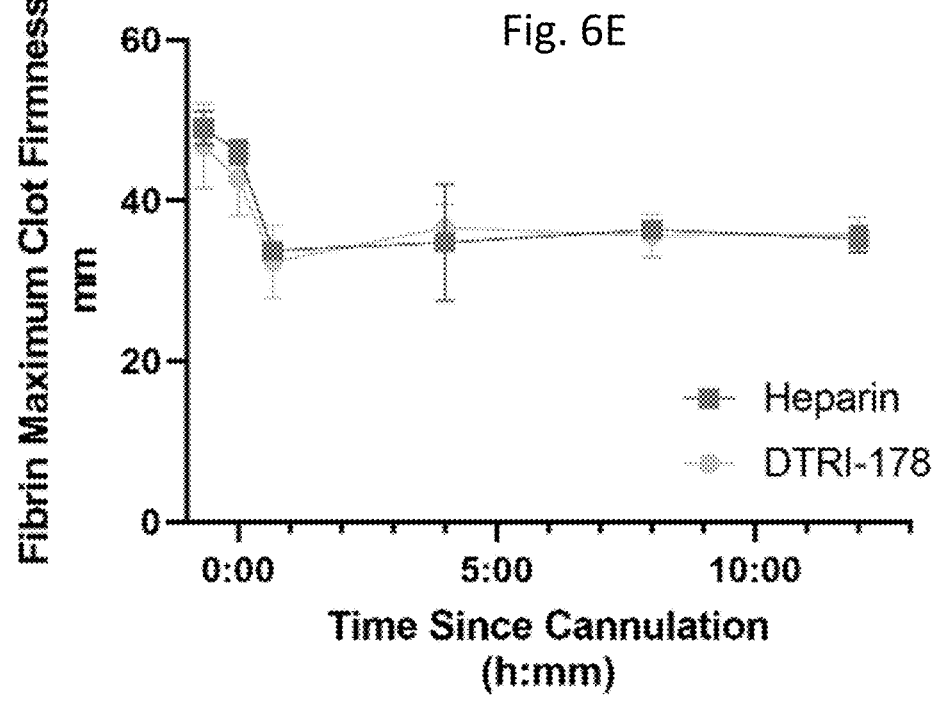
Figure 11:
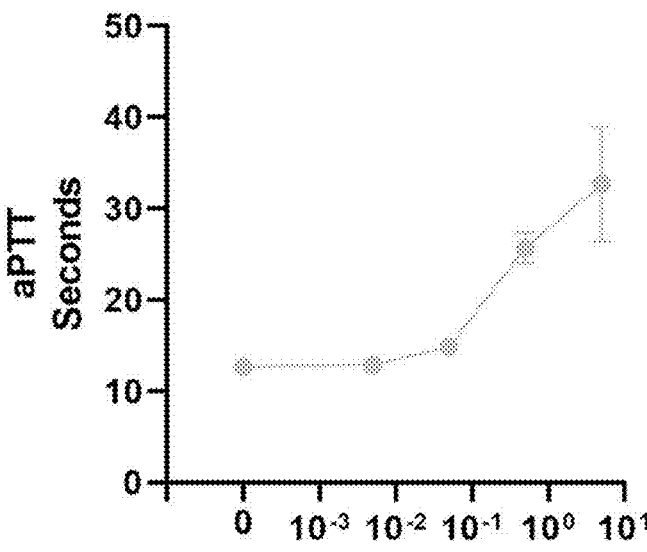
FIG. 11 shows the effect of DTRI-178 on activated partial thromboplastin time (aPTT) in pooled normal porcine plasma. Each point represents the mean of three replicates±standard error of the mean.

Porcine UFH infusion was titrated to the ACT goal of 180-220 s, with a mean ACT across all time points for all animals of 194 s. The aptamer dose required to double the baseline aPTT was about 0.5 µM (FIG. 11). Therefore, the five aptamer-treated piglets received only a single dose at the time of cannulation divided between the animal and circuit for a target plasma concentration of 0.50 µM. The mean dose received based on hematocrit, weight, and dose administered on the day of the procedure resulted in an actual plasma concentration of 0.49 µM. Administration of aptamer to the piglet immediately prior to cannulation resulted in a mean ACT-LR increase of 26.6 s (FIG. 5). This increase was durable across all five runs, with the mean increase persisting at 12 h (105.3±6.2 s versus 129.2±7.8 s, p=0.001573). The mean ACT-LR across all time points after aptamer treatment was 127 s (normal=103 s across all neonatal piglets in our experience).

Aptamer Anticoagulation Spares the Tissue Factor Pathway of Coagulation

Figures 12A, 12B:
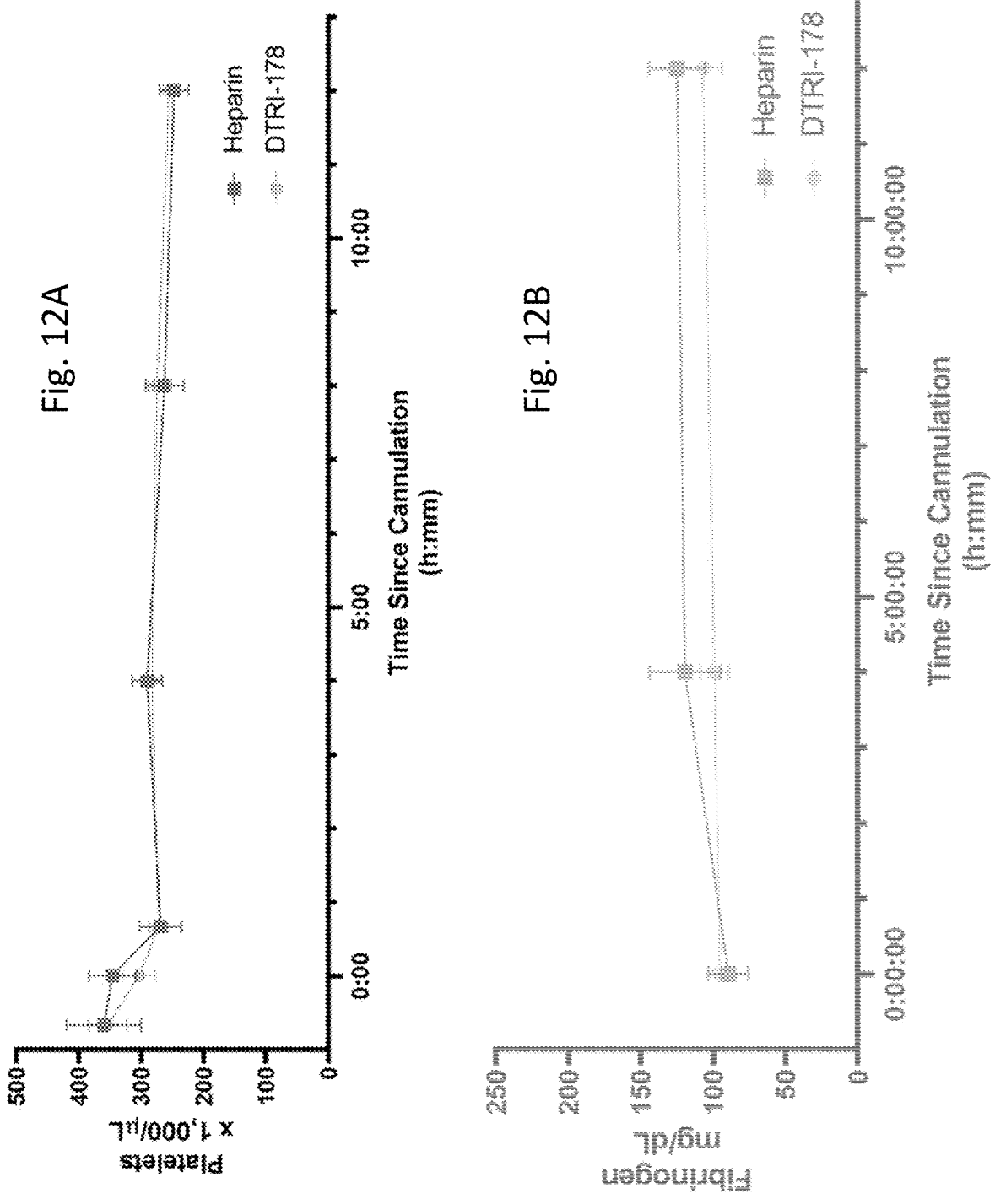
FIGS. 12A-12B show quantitative (FIG. 12A) platelet count and (FIG. 12B) fibrinogen levels at select time-points.

ROTEM provides data similar to (and output parameters analogous to) the older viscoelastic testing technology thromboelastography (TEG). It is a rapid whole-blood assay that quantifies clot formation kinetics and firmness in response to different activation agents. ROTEM samples taken throughout the run confirmed the specificity of the aptamer for the intrinsic pathway of coagulation. As expected, treatment with DTRI-178 resulted in a significant and reproducible increase in INTEM coagulation time (CT), consistent with ACT-LR testing (FIGS. 6A-6E). Specifically, the mean INTEM CT increased from 167.5 s to 385.8 s after bolus of DTRI-178 but before starting ECMO (p=0.002912). ROTEM demonstrated that the extrinsic pathway was spared by both UFH and aptamer, with EXTEM CT unchanged after administration of each (58 s to 55.4 s for UFH, p=0.7125; and 57.3 s to 60.8 s for DTRI-178; p=0.3657). Of note, INTEM testing was not performed for heparinized samples, as the heparin concentrations used in this experiment would result in no clot formation and no calculable CT (45). Instead, the ROTEM heparinase-treated HEPTEM protocol were used to determine if there was an underlying intrinsic coagulopathy. Finally, fibrin-only ROTEM (FIBTEM, which utilizes an extrinsic pathway activator after a cytochalasin D platelet inactivation step) revealed no differences in the trajectory of clot firmness over the 12 hour runs between the two groups. Platelet counts and quantitative fibrinogen testing confirmed similarity between the two groups over each run (FIGS. 12A-12B).

Aptamer in COVID-19 ECMO Patient Samples

Figure 7:
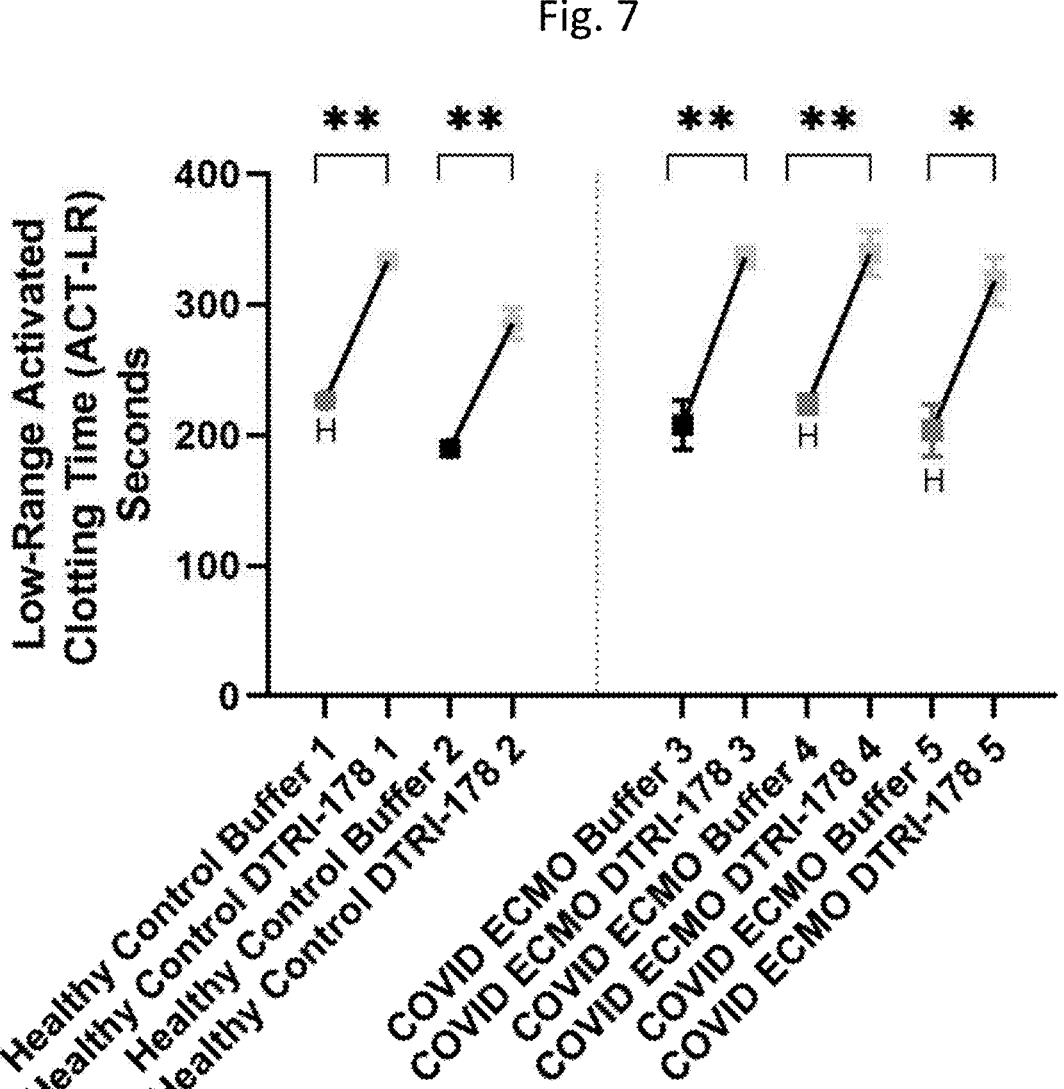
FIG. 7 shows low-range activated clotting time (ACT-LR) analyses of DTRI-178- and buffer-treated blood specimens from two healthy donors and three COVID-19 patients on ECMO. Black and red points represent the baseline ACT-LR from buffer-treated specimens from two healthy donors (left) and three COVID-19 patients on ECMO (right). Turquoise points represent the same specimens after treatment with DTRI-178 for a final concentration of 0.5 μM. All points represent the mean and error bars are ±standard error of the mean. Heparinized healthy donor blood and specimens from therapeutically anticoagulated (with UFH) COVID-19 ECMO patients are highlighted with a red point and "H". There is significant ACT-LR prolongation after addition of DTRI-178 for both healthy donors (Left, healthy controls 1 and 2, p=0.004 and 0.002, respectively). There is a similarly significant prolongation after DTRI-178 addition to COVID ECMO whole blood (p=0.003 for both COVID ECMO 3 and 4; and p=0.013 for COVID ECMO 5).
Figure 8A:
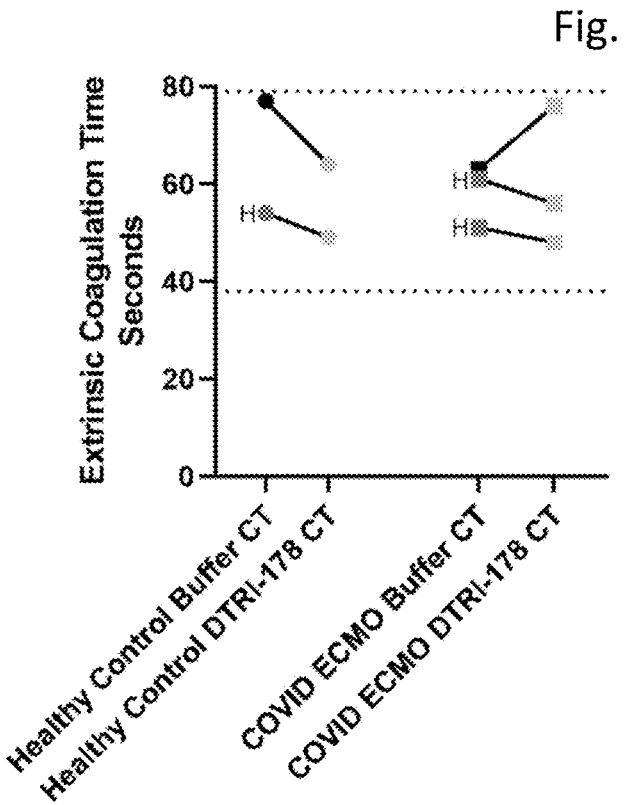
FIGS. 8A-8E show rotational thromboelastometry (ROTEM) analyses of the extrinsic (EXTEM), intrinsic heparinase-treated (HEPTEM), and fibrin-only (FIBTEM) pathways of coagulation of healthy donor blood (n=2) and blood from patients with COVID-19 on ECMO (n=3). Blood was treated with either buffer or DTRI-178 for a final concentration of 0.5 μM, and reference ranges are included as dashed lines. Heparinized healthy donor blood and specimens from COVID-19 ECMO patients therapeutically anticoagulated with UFH are highlighted with a red point and "H".
Figure 8B:
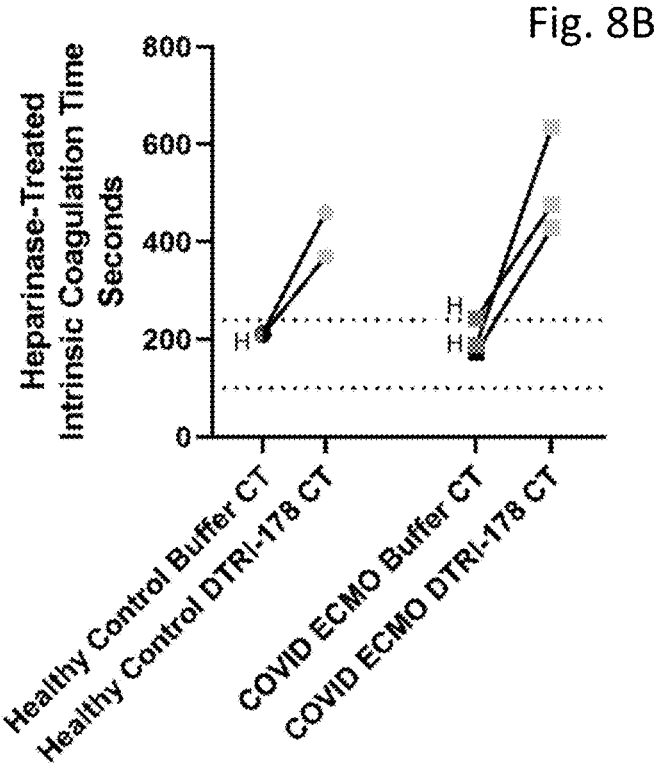
Figures 8C, 8D:
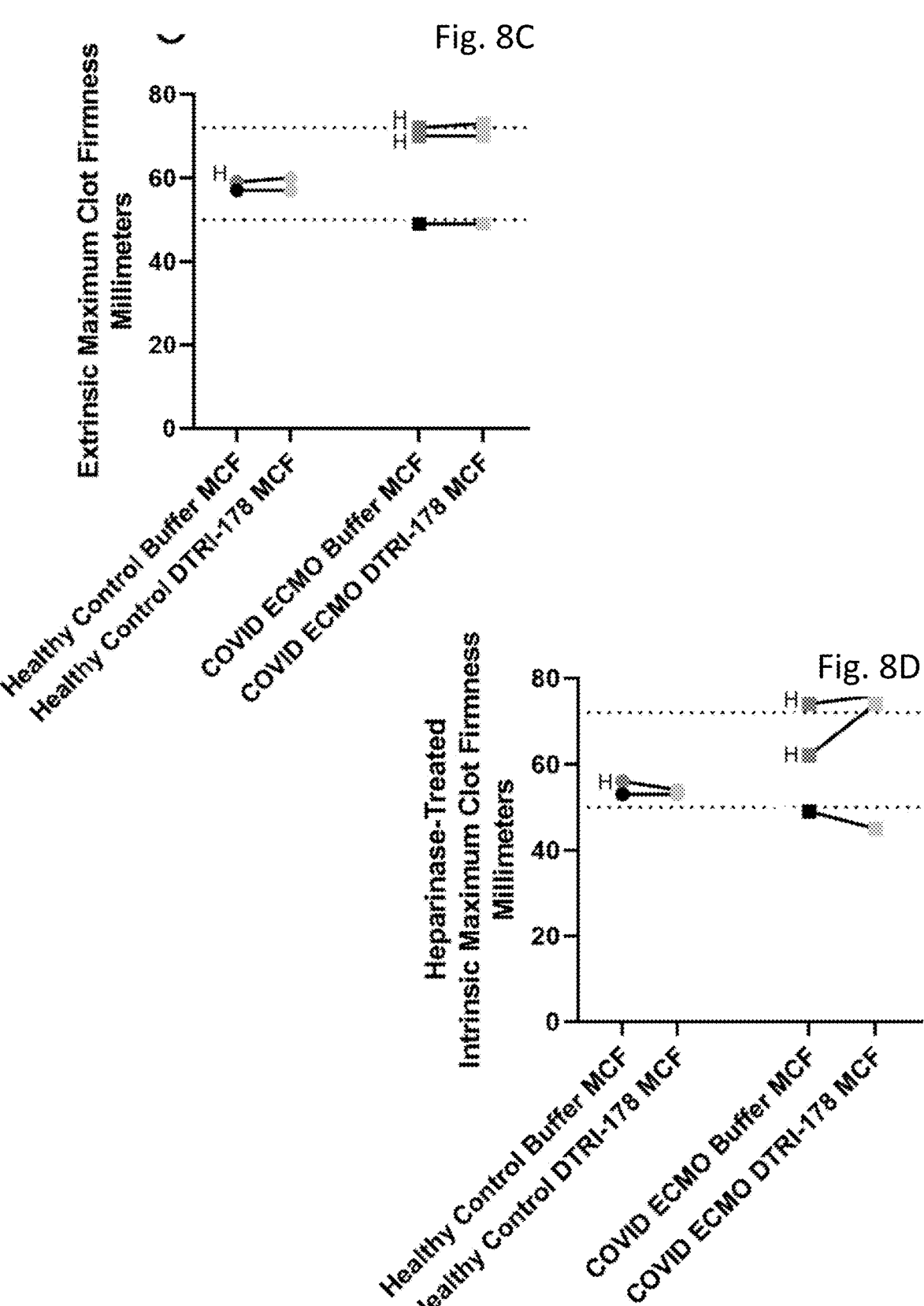
Figure 8E:
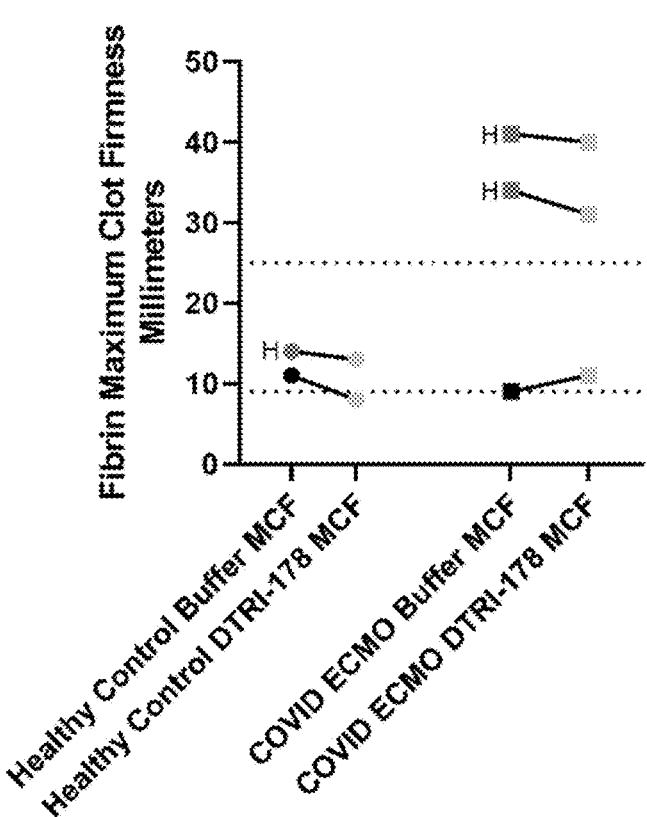

Whole citrated blood was obtained from three adult patients on ECMO for severe hypoxic respiratory failure in the context of COVID-19-related ARDS. Of these, 2/3 were therapeutically anticoagulated using UFH at the time of specimen acquisition (1/3 was off of heparin for >24 hours due to hemorrhagic complications). Whole blood was collected from two healthy adult donors for comparison, with 1/2 specimens anticoagulated with 0.5 U/mL UFH. The ACT-LR was prolonged significantly in both healthy donors after treatment with DTRI-178 (226.5 s and 189.7 s for buffer-treated samples versus 333.0 and 285.3 s for DTRI-178, p=0.004 and 0.002, respectively, FIG. 7). Similarly, ACT-LR was prolonged significantly in blood collected

SUMMARY

The present Examples demonstrate that an anticoagulant agent comprising an RNA aptamer against FIXa maintains circuit patency with superior hemostasis and equivalent thromboprevention compared to UFH in a high-fidelity porcine model of pediatric VA ECMO. This preclinical evidence demonstrates a role for FIXa inhibition in the management of children and adults on ECMO, particularly among those at highest risk for bleeding, clotting, or both (i.e., premature infants, adults with coagulopathy, COVID-19 pneumonia, and trauma victims). This rational approach to anticoagulation may reduce or obviate the need for frequent blood product transfusions, reduce devastating hemorrhagic complications, avoid the risk of HIT, and potentially make ECMO a safer therapy for additional populations of infants and adults for whom the risks of conventional anticoagulation have historically been unacceptably high, including those with severe COVID-19 pneumonia.

---

SEQUENCE LISTING

```
<160> NUMBER OF SEQ ID NOS: 3

<210> SEQ ID NO 1
<211> LENGTH: 34
<212> TYPE: RNA
<213> ORGANISM: Artificial Sequence
<220> FEATURE:
<223> OTHER INFORMATION: Synthetic- Exemplary FIXa aptamer

<400> SEQUENCE: 1
auggggacua uaccgcguaa ugcugccucc ccau                              34

<210> SEQ ID NO 2
<211> LENGTH: 36
<212> TYPE: RNA
<213> ORGANISM: Artificial Sequence
<220> FEATURE:
<223> OTHER INFORMATION: Synthetic- Exemplary FXa aptamer

<400> SEQUENCE: 2
gagagccccA gcgagauaau acuuggcccc gcucuu                            36

<210> SEQ ID NO 3
<211> LENGTH: 58
<212> TYPE: RNA
<213> ORGANISM: Artificial Sequence
<220> FEATURE:
<223> OTHER INFORMATION: Synthetic- Exemplary prothrombin aptamer

<400> SEQUENCE: 3
ggcggucgau cacacaguuc aaacguaaua agccaaugua cgaggcagac gacucgcc     58
```

--- from all three patients with severe COVID-19 and associated respiratory failure on ECMO and then treated with DTRI-178 (p<0.05 in all cases).

ROTEM analysis demonstrated the expected changes of HEPTEM prolongation without effects on HEPTEM MCF (FIGS. 8A-8E). Likewise, no effects were engendered by DTRI-178 on the extrinsic pathway in both the EXTEM and FIBTEM (fibrin-only) tests. This prolongation of the HEPTEM CT with preservation of clot firmness and extrinsic pathway was similar in both the healthy and COVID-19 samples.

We claim:

1. A method for controlling coagulation in a subject in need of extracorporeal membrane oxygenation, the method comprising administering an effective amount of an anticoagulant agent that directly inhibits one or more steps in a coagulation pathway to the subject, wherein the effective amount of the anticoagulant agent is administered as a bolus and controls coagulation during extra corporeal membrane oxygenation for a coagulation control time of at least 4 hours and wherein the anticoagulant agent is an anticoagulant aptamer comprising an oligonucleotide having at least 80% sequence identity to any one of SEQ ID NOS: 1-3.

2. The method of claim 1 further comprising administering a second effective amount of the anticoagulant agent to the subject after the coagulation control time.

3. The method of claim 2, wherein the subject does not receive an administration of the anticoagulant agent during the coagulation control time.

4. The method of claim 2, wherein the second effective amount of the anticoagulant agent is administered as a bolus.

5. The method of claim 1, further comprising prior to administering the anticoagulant agent to the subject determining whether the subject has hypersensitivity to the anticoagulant agent or a component thereof.

6. The method of claim 1, wherein the anticoagulant aptamer is PEGylated.

7. The method of claim 1, wherein the anticoagulant aptamer comprises the oligonucleotide of SEQ ID NO: 1.

8. The method of claim 1, wherein the coagulation control time is characterized by one or more of the following: hematocrit stability, absence of a need for blood transfusion, clinical evidence of hemostasis, absence of clinical signs of bleeding, negligible extracorporeal transmembrane oxygenator pressure gradient, or stable blood flows through the extracorporeal membrane oxygenator.

9. The method of claim 1, wherein the subject is a pediatric subject.

10. The method of claim 1, wherein the subject is in need of a treatment for cardiopulmonary failure.

11. The method of claim 1, wherein the subject is in need of a treatment for a severe acute respiratory syndrome.

12. The method of claim 11, wherein the subject has SARS-COV-2 infection.

13. The method of claim 1, wherein the anticoagulant agent comprises an aptamer that inhibits one of more steps in the contact coagulation pathway.

14. The method of claim 1, wherein the anticoagulant agent inhibits one of more of Factor IX, Factor X, Factor XI, Factor XII, or an activated form thereof.

15. The method of claim 1, wherein the anticoagulant agent comprises DTRI-178.

* * * * *